(12) United States Patent
Chalana et al.

(10) Patent No.: US 7,727,150 B2
(45) Date of Patent: *Jun. 1, 2010

(54) SYSTEMS AND METHODS FOR DETERMINING ORGAN WALL MASS BY THREE-DIMENSIONAL ULTRASOUND

(75) Inventors: Vikram Chalana, Mill Creek, WA (US); Stephen Dudycha, Bothell, WA (US); Jongtae Yuk, Redmond, WA (US); Gerald McMorrow, Kirkland, WA (US)

(73) Assignee: Verathon Inc., Bothell, WA (US)

( * ) Notice: Subject to any disclaimer, the term of this patent is extended or adjusted under 35 U.S.C. 154(b) by 1150 days.

This patent is subject to a terminal disclaimer.

(21) Appl. No.: 11/295,043

(22) Filed: Dec. 6, 2005

(65) Prior Publication Data

US 2007/0004983 A1    Jan. 4, 2007

Related U.S. Application Data

(63) Continuation-in-part of application No. 11/213,284, filed on Aug. 26, 2005, and a continuation-in-part of application No. 11/119,355, filed on Apr. 29, 2005, now Pat. No. 7,520,857, and a continuation-in-part of application No. 11/061,867, filed on Feb. 17, 2005, now Pat. No. 7,611,466, and a continuation-in-part of application No. 10/888,735, filed on Jul. 9, 2004, now abandoned, and a continuation-in-part of application No. 10/704,966, filed on Nov. 12, 2003, now Pat. No. 6,803,308, and a continuation-in-part of application No. 10/701,955, filed on Nov. 5, 2003, now Pat. No. 7,087,022, which is a continuation-in-part of application No. 10/443,126, filed on May 20, 2003, now Pat. No. 7,041,059, application No. 11/295,043, which is a continuation-in-part of application No. PCT/US03/24368, filed on Aug. 1, 2003, and a continuation-in-part of application No. 10/633,186, filed on Jul. 31, 2003, now Pat. No. 7,004,904, and a continuation-in-part of application No. 10/607,919, filed on Jun. 27, 2003, now Pat. No. 6,884,217, and a continuation-in-part of application No. PCT/US03/14785, filed on May 9, 2003, which is a continuation of application No. 10/165,556, filed on Jun. 7, 2002, now Pat. No. 6,676,605.

(60) Provisional application No. 60/470,525, filed on May 12, 2003, provisional application No. 60/423,881, filed on Nov. 5, 2002, provisional application No. 60/400,624, filed on Aug. 2, 2002, provisional application No. 60/545,576, filed on Feb. 17, 2004, provisional application No. 60/633,485, filed on Dec. 6, 2004, provisional application No. 60/566,818, filed on Apr. 30, 2004, provisional application No. 60/566,127, filed on Apr. 30, 2004.

(51) Int. Cl.
*A61B 8/00* (2006.01)

(52) U.S. Cl. .................. 600/437; 600/438; 600/458; 600/459; 606/3

(58) Field of Classification Search .................. 600/437, 600/438, 458, 460, 459; 606/3
See application file for complete search history.

(56) References Cited

U.S. PATENT DOCUMENTS

| | | | |
|---|---|---|---|
| 5,235,985 | A | 8/1993 | McMorrow |
| 5,698,549 | A | 12/1997 | Steers |
| 5,908,390 | A | 6/1999 | Matsushima |
| 5,964,710 | A | 10/1999 | Ganguly |
| 6,110,111 | A | 8/2000 | Barnard |
| 6,213,949 | B1 | 4/2001 | Ganguly |
| 6,406,431 | B1 * | 6/2002 | Barnard et al. ............. 600/443 |
| 6,443,894 | B1 | 9/2002 | Sumanaweera et al. |
| 6,511,426 | B1 | 1/2003 | Hossack et al. |
| 6,676,605 | B2 | 1/2004 | Barnard |
| 6,755,787 | B2 | 6/2004 | Hossack et al. |

OTHER PUBLICATIONS

Naya et al., Intraobserver and Interobserver Variance in the Measurment of Ultrasound-Estimated Bladder Weight, Dept. of Urology, Kyoto Prefectural University of Medicine.

Kuzmic, Brkljacic & Ivankovic, Sonographic Measurement of Detrusor Muscle Thickness in Healthy Children, Pediatr Nephrol (2001) 16:1122-1125.

Muller, Jacobsson, Marild & Hellstrom, Detrusor Thickness in Healthy Children Assessed by a Standardized Ultrasound Method, The Journal of Uriology vol. 166, 2364-2367.

Muller et al., Standardized Ultrasound Method for Assessing Detrusor Muscle Thickness in Children, The Journal of Uriology, vol. 164, 134-138.

Kuzmic et al., Ultrasound Assessment of Detrusor Muscle Thickness in Children with Non-neuropathic Bladder/Sphincter Dysfunction, European Urology 41, (2002) 214-219.

Kojima et al., Ultrasonic Estimation of Bladder Weight as a Measur of Bladder Hypertrophy in Men with Infravesical Obstruction: A Priliminary Report, Dept. of Urology, Kyoto.

Kojima et al, Reversible Change of Bladder Hypertrophy due to Benign Prostatic Hyperplasia After Surgical Relief of Obstruction, Journal of Urology, vol. 158, 89-93.

Manieri et al., The Diagnosis of Bladder Outlet Obstruction in Men by Ultrasound Measurement of Bladder Wall Thickness, The Journal of Urology, vol. 159, 761-765.

Miyashita et al., Ultrasonic Measurement of Bladder Weight as a Possible Predictor of Acute Urinary Retention in Men with Lower Urinary Tract Symptoms Suggestive of Benign.

Oelke, Hofner, Wiese, Grunewald & Jonas, Increase in Detrusor Wall Thickness Indicates Bladder Outlet Obstruction (BOO) in Men, World J Urol (2002) 19: 443-452.

* cited by examiner

*Primary Examiner*—Brian Casler
*Assistant Examiner*—Joel M Lamprecht
(74) *Attorney, Agent, or Firm*—Black Lowe & Graham

(57) ABSTRACT

An ultrasound system and method to measure an organ wall weight and mass. When the organ is a bladder, a bladder weight (UEBW) is determined using three-dimensional ultrasound imaging that is acquired using a hand-held or machine controlled ultrasound transceiver. The infravesical region of the bladder is delineated on this 3D data set to enable the calculation of urine volume and the bladder surface area. The outer anterior wall of the bladder is delineated to enable the calculation of the bladder wall thickness (BWT). The UEBW is calculated as a product of the bladder surface area, the bladder wall thickness, and the bladder wall specific gravity.

27 Claims, 27 Drawing Sheets

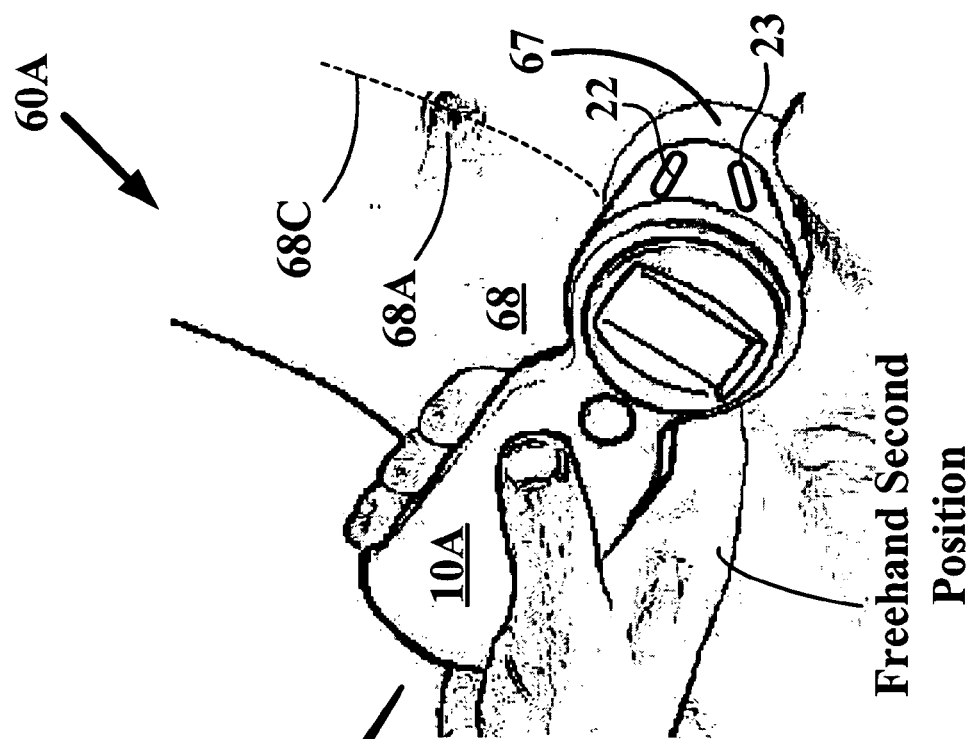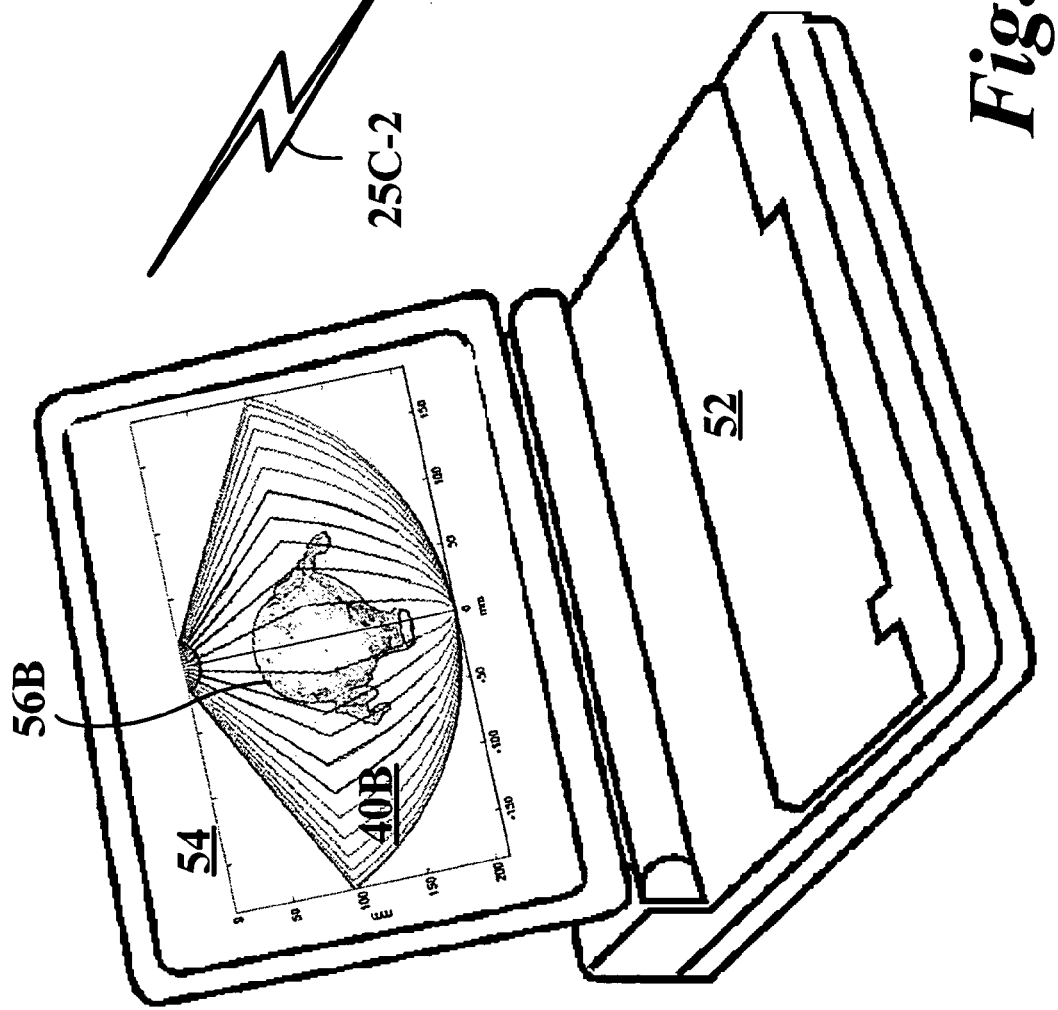
Fig. 6

SYSTEMS AND METHODS FOR DETERMINING ORGAN WALL MASS BY THREE-DIMENSIONAL ULTRASOUND

PRIORITY CLAIM

This application claims priority to U.S. provisional patent application Ser. No. 60/633,485 filed Dec. 6, 2004.

This application is a continuation-in-part of and claims priority to U.S. patent application Ser. No. 11/213,284 filed Aug. 26, 2005.

This application claims priority to and is a continuation-in-part of U.S. patent application Ser. No. 11/119,355 filed Apr. 29, 2005 now U.S. Pat. No. 7,520,857, which claims priority to U.S. provisional patent application Ser. No. 60/566,127 filed Apr. 30, 2004. This application also claims priority to and is a continuation-in-part of U.S. patent application Ser. No. 10/701,955 filed Nov. 5, 2003 now U.S. Pat. No. 7,087,022, which in turn claims priority to and is a continuation-in-part of U.S. patent application Ser. No. 10/443,126 filed May 20, 2003 now U.S. Pat. No. 7,041,059.

This application claims priority to and is a continuation-in-part of U.S. patent application Ser. No. 11/061,867 filed Feb. 17, 2005 now U.S. Pat. No. 7,611,466, which claims priority to U.S. provisional patent application Ser. No. 60/545,576 filed Feb. 17, 2004 and U.S. provisional patent application Ser. No. 60/566,818 filed Apr. 30, 2004.

This application is also a continuation-in-part of and claims priority to U.S. patent application Ser. No. 10/704,966 filed Nov. 12, 2003 now U.S. Pat. No. 6,803,308.

This application claims priority to and is a continuation-in-part of U.S. patent application Ser. No. 10/607,919 filed Jun. 27, 2003 now U.S. Pat. No. 6,884,217.

This application is a continuation-in-part of and claims priority to PCT application serial number PCT/US03/24368 filed Aug. 1, 2003, which claims priority to U.S. provisional patent application Ser. No. 60/423,881 filed Nov. 5, 2002 and U.S. provisional patent application Ser. No. 60/400,624 filed Aug. 2, 2002.

This application is also a continuation-in-part of and claims priority to PCT Application Serial No. PCT/US03/14785 filed May 9, 2003, which is a continuation of U.S. patent application Ser. No. 10/165,556 filed Jun. 7, 2002 now U.S. Pat. No. 6,676,605.

This application is also a continuation-in-part of and claims priority to U.S. patent application Ser. No. 10/888,735 filed Jul. 9, 2004 now abandoned.

This application is also a continuation-in-part of and claims priority to U.S. patent application Ser. No. 10/633,186 filed Jul. 31, 2003 now U.S. Pat. No. 7,004,904 which claims priority to U.S. provisional patent application Ser. No. 60/423,881 filed Nov. 5, 2002 and to U.S. patent application Ser. No. 10/443,126 filed May 20, 2003 which claims priority to U.S. provisional patent application Ser. No. 60/423,881 filed Nov. 5, 2002 and to U.S. provisional application 60/400,624 filed Aug. 2, 2002. This application also claims priority to U.S. provisional patent application Ser. No. 60/470,525 filed May 12, 2003, and to U.S. patent application Ser. No. 10/165,556 filed Jun. 7, 2002. All of the above applications are herein incorporated by reference in their entirety as if fully set forth herein.

FIELD OF THE INVENTION

This invention relates generally to ultrasound-based diagnostic systems and procedures.

BACKGROUND OF THE INVENTION

Benign prostate hyperplasia (BPH) and other disorders can cause mechanical bladder outlet obstruction (BOO). A marker for predicting BOO is determining the weight of the bladder wall. Using probing ultrasound, an ultrasound estimated bladder wall weight (UEBW) might be obtained in a non-invasive way. Existing methods for acquiring UEBW assumes that the bladder is spherically shaped and that the thickness of the bladder wall is relatively constant in near empty to nearly full bladders. Moreover, the existing 2D methods are manually based, utilizing leading edge-to-leading edge of opposing bladder walls laboriously executed upon a series of two-dimensional images, and are fraught with analytical inaccuracies (H. Miyashita, M. Kojima, and T. Miki, "Ultrasonic measurement of bladder weight as a possible predictor of acute urinary retention in men with lower urinary tract symptoms suggestive of benign prostate hyperplasia", *Ultrasound in Medicine and Biology* 2002, 28(8): 985-990; M. Oelke, K. Hofner, B. Wiese, V. Gruneweld, and U. Jonas, "Increase in detrusor wall thickness indicates bladder outlet obstruction in men," *World J. of Urology*, 2002, 19(6), 443-452; L. Muller, T. Bergstrom, M. Hellstrom, E. Svensson, and B. Jacobson, *"Standardized ultrasound method for assessing detrusor muscle thickness in children,"* J. Urol., 200, 164: 134-138; and Naya, M. Kojima, H. Honjyo, A. Ochiai, O. Ukimura, and H. Watanabe, "Intraobserver and interobserver variance in the measurement of ultrasound-estimated bladder weight," *Ultrasound in Med. & Biol.*, 1999, 24(5): 771-773).

There is a need to accurately and non-invasively determine bladder wall weight by accurately measuring bladder wall volume to avoid incurring the errors invoked by the fixed bladder shape assumptions and those generated by the manual image processing methods of 2D acquired ultrasound images.

SUMMARY OF THE INVENTION

A method and system to acquire an ultrasound-estimated organ wall mass or weight from three dimensional ultrasound echo information is disclosed.

BRIEF DESCRIPTION OF THE DRAWINGS

Embodiments of the present invention are described in detail below with reference to the following drawings.

FIG. 6 depicts images showing the patient being scanned by the transceiver and the data being wirelessly uploaded to a personal computer of a properly targeted ROI in the abdominal area;

DETAILED DESCRIPTION OF THE PREFERRED EMBODIMENTS

Figure 1:
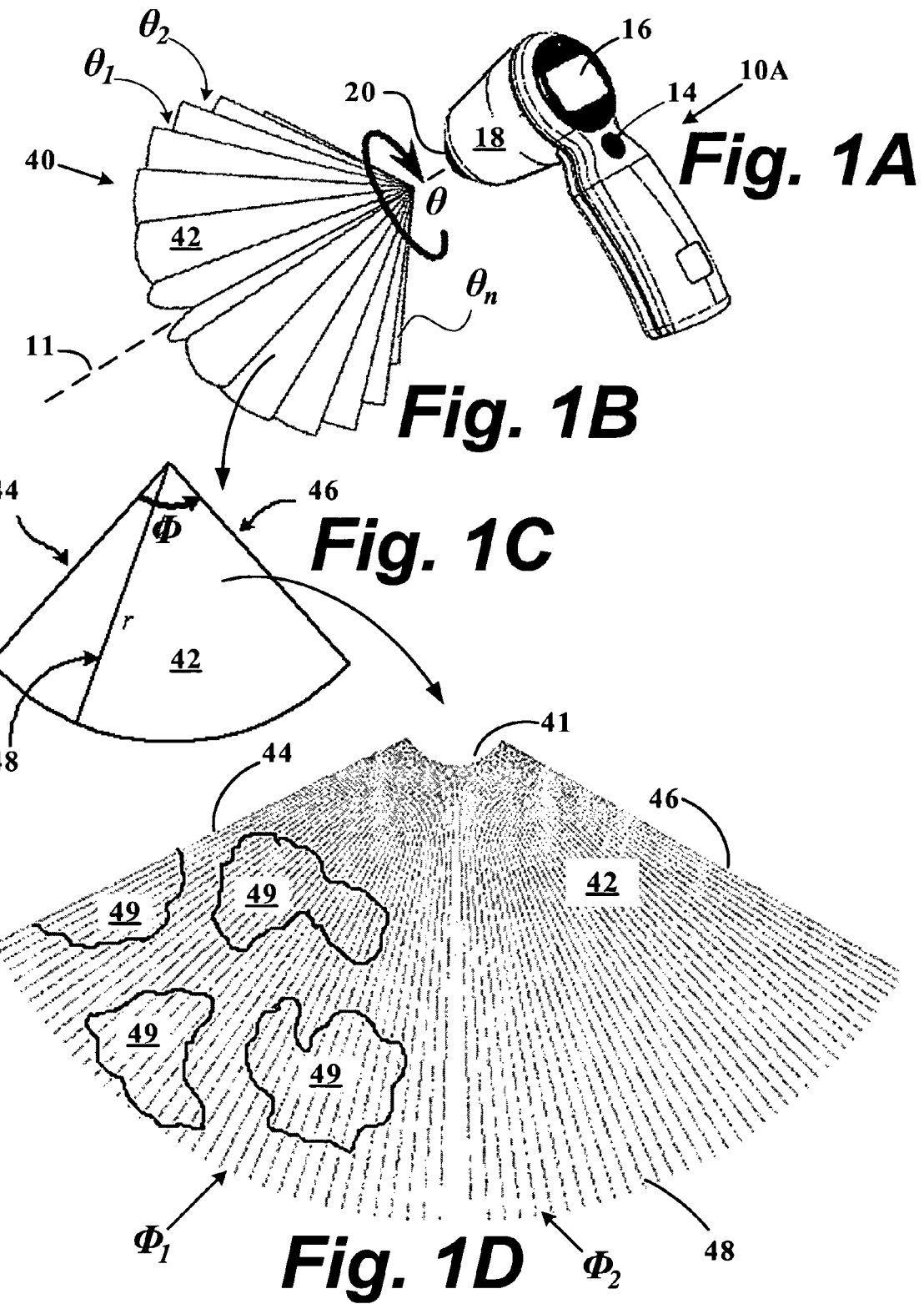
FIGS. 1A-D depicts a partial schematic and a partial isometric view of a transceiver, a scan cone comprising a rotational array of scan planes, and a scan plane of the array.

Methods and systems to acquire an ultrasound estimated organ wall mass and/or weight such as a bladder using three dimensional ultrasound echo information are described. The three-dimensional (3D) based ultrasound information is generated from a microprocessor-based system utilizing an ultrasound transceiver that properly targets the organ or other region of interest (ROI) and utilizes algorithms to delineate the inner (sub-mucosal) and outer (sub-serosal) wall boundaries of the organ wall as part of a process to determine the organ wall weight or mass. When the organ is a bladder, bladder wall algorithms operate without making geometric assumptions of the bladder so that the shape, area, and thickness between the sub-mucosal and subserosal layers of the bladder wall are more accurately determined to provide in a turn a more accurate determination of the bladder wall volume. Knowing the accurate bladder volume allows a more accurate determination of bladder wall weight or mass as a product of bladder wall volume and bladder wall density or specific gravity.

The embodiments include a system and methods for an automatic and convenient procedures to obtain an estimated bladder weight (UEBW) and/or a mass of the bladder wall based on analysis of three-dimensional images and analysis of one and two-dimensional information that comprises the 3D image. In one particular embodiment, a subject or patient is scanned using an ultrasound transceiver. The ultrasound transceiver, similar to the BladderScan® BVM6500 marketed by Diagnostic Ultrasound Incorporated of Redmond, Wash. provides an ultrasound sound image in the form of a three-dimensional scan cone. The 3D scan cone provides images of the ultrasound-probed ROI in the form of a rotational 2D scan plane array and is referred to as a V-mode® image or images. The V-mode® images may also be include wedge and translational arrays.

After the scan, the transceiver displays the volume of urine retained within the bladder along with aiming information for the transceiver to enable the correct placement of the probe with respect to the bladder. The aiming information allows the user to repeat the scan as needed to get a well-centered image and/or a complete image of the bladder.

Once the scan is complete, the three-dimensional data may be transmitted securely to a server computer on a remote computer that is coupled to a network, such as the Internet. Alternately, a local computer network, or an independent standalone personal computer may also be used. In any case, image processing algorithms on the computer analyze pixels within a 2D portion of a 3D image or the voxels of the 3D image. The image processing algorithms then define which pixels or voxels occupy or otherwise constitute an inner or outer wall layer. Thereafter, wall areas of the inner and outer layers, and thickness between them, is determined. Organ wall or bladder wall weight is determined as a product of wall layer area, thickness between the wall layers, and density of the wall.

The image processing algorithms delineate the outer and inner walls of the anterior portion of bladder wall within the bladder region and determine the actual surface area, S, of the bladder wall using, for example, a modification of the Marching Cubes algorithm, as utilized from the VTK Library maintained by Kitware, Inc. (Clifton Park, N.Y., USA), incorporated by reference herein. The bladder wall thickness, t, is then calculated as the distance between the outer and the inner surfaces of bladder wall. Finally, as shown in equation E1, the bladder weight is estimated as the product of the surface area, thickness and bladder muscle specific gravity, $\rho$:

$$UEBW = S \times t \times \rho. \quad \text{E1:}$$

One benefit of the embodiments of the present invention is that it produces more accurate and consistent estimates of UEBW. The reasons for higher accuracy and consistency include:

1. The use of three-dimensional data instead of two-dimensional data to calculate the surface area and thickness. In another embodiment, the outer anterior wall of the bladder is delineated to enable the calculation of the bladder wall thickness (BWT);

2. The use of the measured surface area instead of using surface area based upon a spherical model; and
3. The automatic and consistent measurement of the bladder wall thickness.

Additional benefits conferred by the embodiments also include its non-invasiveness and its ease of use in that UEBW is measured over a range of bladder volumes, thereby eliminating the need to catheterize the patient to fill up to a fixed volume.

FIGS. 1A-D depicts a partial schematic and partial isometric view of a transceiver, a scan cone array of scan planes, and a scan plane of the array.

FIG. 1A depicts a transceiver 10A having an ultrasound transducer housing 18 and a transceiver dome 20 from which ultrasound energy emanates to probe a patient or subject. Information from ultrasound echoes returning from the probing ultrasound is presented on the display 14. The information may be alphanumeric, pictorial, and describe positional locations of a targeted organ or ROI.

FIG. 1B is a graphical representation of a plurality of scan planes 42 that contain the probing ultrasound. The plurality of scan planes 42 defines a scan cone 40 in the form of a three-dimensional (3D) array having a substantially conical shape that projects outwardly from the dome 20 of the transceivers 10A.

The plurality of scan planes 42 are oriented about an axis 11 extending through the transceivers 10A. One or more, or alternately each of the scan planes 42 are positioned about the axis 11, which may be positioned at a predetermined angular position θ. The scan planes 42 are mutually spaced apart by angles $\theta_1$ and $\theta_2$ whose angular value may vary. That is, although the angles $\theta_1$ and $\theta_2$ to $\theta_n$ are depicted as approximately equal, the θ angles may have different values. Other scan cone configurations are possible. For example, a wedge-shaped scan cone, or other similar shapes may be generated by the transceiver 10A.

FIG. 1C is a graphical representation of a scan plane 42. The scan plane 42 includes the peripheral scan lines 44 and 46, and an internal scan line 48 having a length r that extends outwardly from the transceivers 10A and between the scan lines 44 and 46. Thus, a selected point along the peripheral scan lines 44 and 46 and the internal scan line 48 may be defined with reference to the distance r and angular coordinate values φ and θ. The length r preferably extends to approximately 18 to 20 centimeters (cm), although other lengths are possible. Particular embodiments include approximately seventy-seven scan lines 48 that extend outwardly from the dome 20, although any number of scan lines may be used.

FIG. 1D a graphical representation of a plurality of scan lines 48 emanating from the ultrasound transceiver forming a single scan plane 42 extending through a cross-section of portions of an internal bodily organ. The scan plane 42 is fan-shaped, bounded by peripheral scan lines 44 and 46, and has a semi-circular dome cutout 41. The number and location of the internal scan lines emanating from the transceivers 10A within a given scan plane 42 may be distributed at different positional coordinates about the axis line 11 as required to sufficiently visualize structures or images within the scan plane 42. As shown, four portions of an off-centered region-of-interest (ROI) are exhibited as irregular regions 49 of the internal organ. Three portions are viewable within the scan plane 42 in totality, and one is truncated by the peripheral scan line 44.

As described above, the angular movement of the transducer may be mechanically effected and/or it may be electronically or otherwise generated. In either case, the number of lines 48 and the length of the lines may vary, so that the tilt angle φ (FIG. 1C) sweeps through angles approximately between −60° and +60° for a total arc of approximately 120°. In one particular embodiment, the transceiver 10A is configured to generate approximately about seventy-seven scan lines between the first limiting scan line 44 and a second limiting scan line 46. In another particular embodiment, each of the scan lines has a length of approximately about 18 to 20 centimeters (cm). The angular separation between adjacent scan lines 48 (FIG. 1B) may be uniform or non-uniform. For example, and in another particular embodiment, the angular separation $\phi_1$ and $\phi_2$ to $\phi_n$ (as shown in FIG. 1B) may be about 1.5°. Alternately, and in another particular embodiment, the angular separation $\phi_1$, $\phi_2$, $\phi_n$ may be a sequence wherein adjacent angles are ordered to include angles of 1.5°, 6.8°, 15.5°, 7.2°, and so on, where a 1.5° separation is between a first scan line and a second scan line, a 6.8° separation is between the second scan line and a third scan line, a 15.5° separation is between the third scan line and a fourth scan line, a 7.2° separation is between the fourth scan line and a fifth scan line, and so on. The angular separation between adjacent scan lines may also be a combination of uniform and non-uniform angular spacings, for example, a sequence of angles may be ordered to include 1.5°, 1.5°, 1.5°, 7.2°, 14.3°, 20.2°, 8.0°, 8.0°, 8.0°, 4.3°, 7.8°, and so on.

Figure 2:
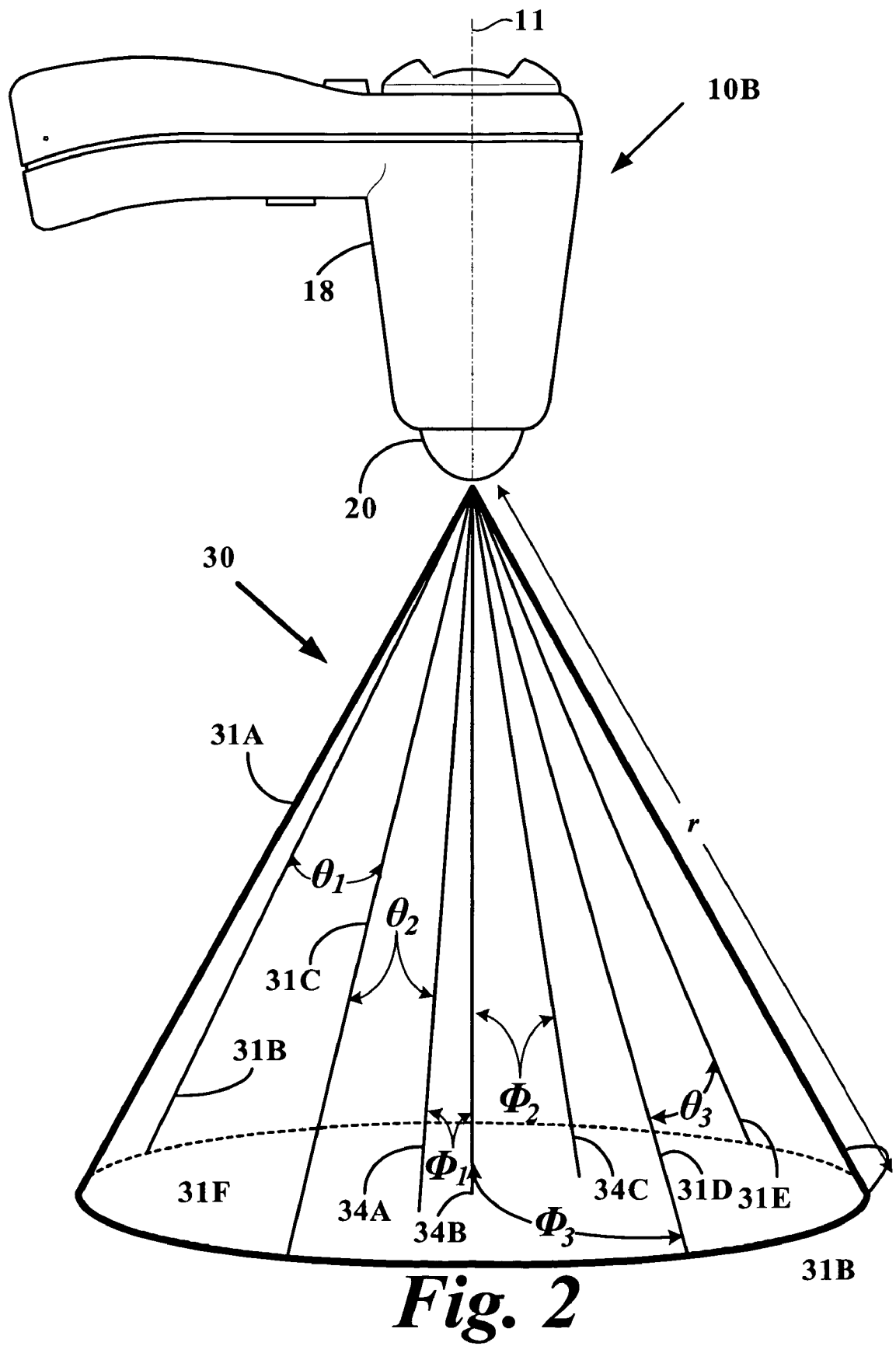
FIG. 2 depicts a partial schematic and partial isometric and side view of a transceiver, and a scan cone array comprised of 3D-distributed scan lines.

FIG. 2 depicts a partial schematic and partial isometric and side view of a transceiver 10B, and a scan cone array 30 comprised of 3D-distributed scan lines. Each of the scan lines have a length r that projects outwardly from the transceiver 10B. As illustrated the transceiver 10B emits 3D-distributed scan lines within the scan cone 30 that are one-dimensional ultrasound A-lines. Taken as an aggregate, these 3D-distributed A-lines define the conical shape of the scan cone 30. The ultrasound scan cone 30 extends outwardly from the dome 20 of the transceiver 10B and centered about the axis line 11 (FIG. 1B). The 3D-distributed scan lines of the scan cone 30 include a plurality of internal and peripheral scan lines that are distributed within a volume defined by a perimeter of the scan cone 30. Accordingly, the peripheral scan lines 31A-31F define an outer surface of the scan cone 30, while the internal scan lines 34A-34C are distributed between the respective peripheral scan lines 31A-31F. Scan line 34B is generally collinear with the axis 11, and the scan cone 30 is generally and coaxially centered on the axis line 11.

The locations of the internal and peripheral scan lines may be further defined by an angular spacing from the center scan line 34B and between internal and peripheral scan lines. The angular spacing between scan line 34B and peripheral or internal scan lines are designated by angle Φ and angular spacings between internal or peripheral scan lines are designated by angle Ø. The angles $\Phi_1$, $\Phi_2$, and $\Phi_3$ respectively define the angular spacings from scan line 34B to scan lines 34A, 34C, and 31D. Similarly, angles $Ø_1$, $Ø_2$, and $Ø_3$ respectively define the angular spacing between scan line 31B and 31C, 31C and 34A, and 31D and 31E.

With continued reference to FIG. 2, the plurality of peripheral scan lines 31A-E and the plurality of internal scan lines 34A-D are three dimensionally distributed A-lines (scan lines) that are not necessarily confined within a scan plane, but instead may sweep throughout the internal regions and along the periphery of the scan cone 30. Thus, a given point within the scan cone 30 may be identified by the coordinates r, Φ, and Ø whose values generally vary. The number and location of the internal scan lines 34A-D emanating from the transceiver 10B may thus be distributed within the scan cone 30 at different positional coordinates as required to sufficiently visualize structures or images within a region of interest (ROI) in a patient. The angular movement of the ultrasound transducer within the transceiver 10B may be mechanically effected, and/or it may be electronically generated. In any case, the number of lines and the length of the lines may be uniform or otherwise vary, so that angle Φ may sweep through angles approximately between −60° between scan line 34B and 31A, and +60° between scan line 34B and 31B. Thus, the angle Φ may include a total arc of approximately 120°. In one embodiment, the transceiver 10B is configured to generate a plurality of 3D-distributed scan lines within the scan cone 30 having a length r of approximately 18 to 20 centimeters (cm).

Figure 3:
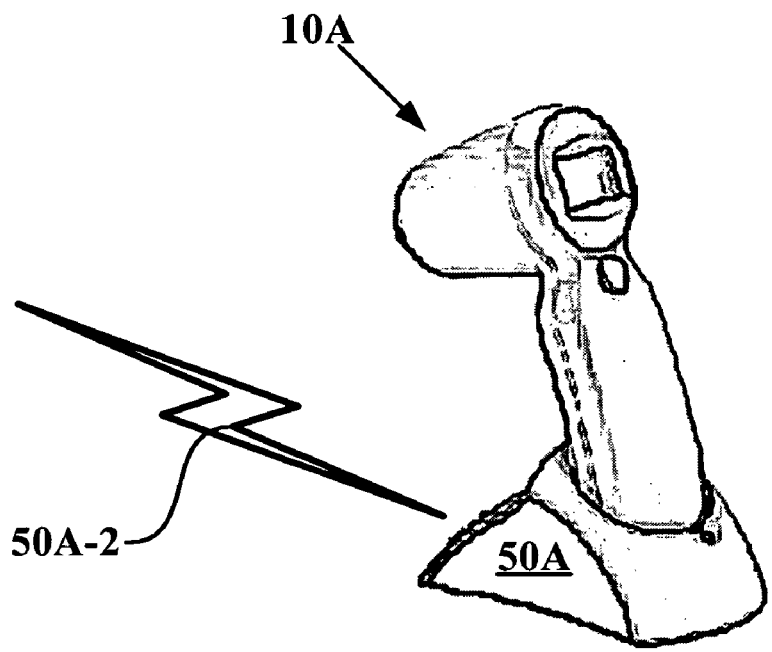
FIG. 3 depicts an ultrasound transceiver housed in a communications cradle and the data being wirelessly uploaded.

FIG. 3 depicts the transceiver 10A (FIG. 1) removably positioned in a communications cradle 50A that is operable to communicate the data wirelessly uploaded to the computer or other microprocessor device (not shown). The data is uploaded securely to the computer or to a server via the computer where it is processed by a bladder weight estimation algorithm that will be described in greater detail below. The transceiver 10B may be similarly housed in the cradle 50A. In this wireless embodiment, the cradle 50A has circuitry that receives and converts the informational content of the scan cone 40 or scan cone 30 to a wireless signal 50A-2.

Figure 4:
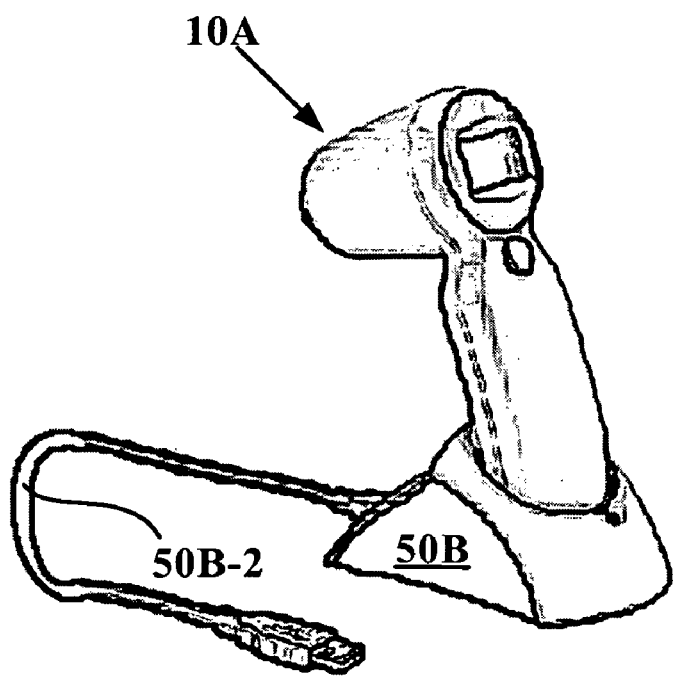
FIG. 4 depicts an ultrasound transceiver housed in a communications cradle where the data uploaded by electrical connection.

FIG. 4 depicts the transceiver 10A removably positioned in a communications cradle 50B where the data is uploaded by an electrical connection 50B-2 to the computer or other microprocessor device (not shown). The data is uploaded securely to the computer or to a server via the computer where it is processed by the bladder weight estimation algorithm. The transceiver 10B may be similarly removably positioned in the cradle 50B. In this embodiment, the cradle 50B has circuitry that receives and converts the informational content of the scan cone 40 or the scan cone 30 to a non-wireless signal that is conveyed in conduit 50B-2 capable of transmitting electrical, light, or sound-based signals. A particular electrical embodiment of conduit 50B-2 may include a universal serial bus (USB) in signal communication with a microprocessor-based device.

Figure 5:
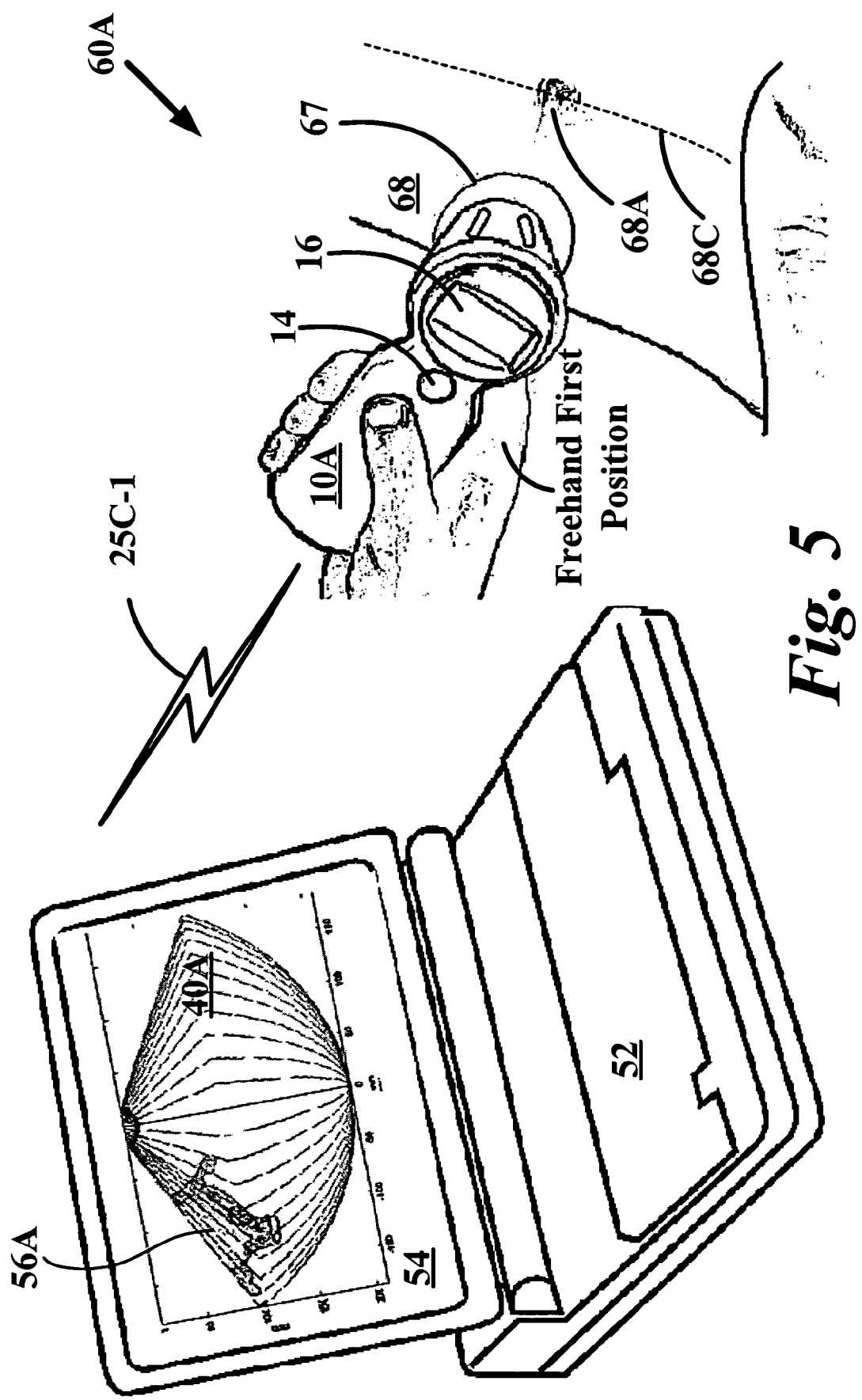
FIG. 5 depicts images showing the abdominal area of a patient being scanned by a transceiver and the data being wirelessly uploaded to a personal computer during initial targeting of a region of interest (ROI)

FIG. 5 depicts images showing the abdominal area of a patient 68 being scanned by a transceiver 10C and the data being wirelessly uploaded to a personal computer during initial targeting of a region of interest (ROI) that is left of the umbilicus 68 and umbilicus midline 68C. FIG. 5 depicts images showing the patient 68 being scanned by a bladder wall mass system 60A during an initial targeting phase using the transceiver 10C capable of generating wireless signal. The transceiver 10C has circuitry that converts the informational content of the scan cone 40 or scan cone 30 to wireless signal 25C-1 that may be in the form of visible light, invisible light (such as infrared light) or sound-based signals. As depicted, the data is wirelessly uploaded to the personal computer 52 during initial targeting of an organ or ROI. In a particular embodiment of the transceiver 10C, a focused 3.7 MHz single element transducer is used that is steered mechanically to acquire a 120-degree scan cone 42. On a display screen 54 coupled to the computer 52, a scan cone image 40A displays an off-centered view of the organ 56A that is truncated.

The scan protocol for obtaining a UEBW begins by placing the transceiver 10C approximately one inch above the symphysis pubis with the scanhead aimed slightly towards the coccyx. The three-dimensional ultrasound data is collected upon pressing the scan button on the scanner. After the scan is complete, the display 14 on the device 10C displays aiming information in the form of arrows. A flashing arrow indicates to the user to point the device in the arrow's direction and rescan. The scan is repeated until the device displays only a solid arrow or no arrow. The display 16 on the device may also display the calculated bladder volume. The aforementioned aiming process is more fully described in U.S. Pat. No. 6,884,217 to McMorrow et al., which is incorporated by reference as if fully disclosed herein. For the UEBW measurement, the required bladder volume is between 200 and 400 ml. If the bladder volume reading is less than 200 ml, the patient could be given some fluids and scanned after a short time interval. Once the scanning is complete and the patient has bladder volume between 200 and 400 ml, the device may be placed on a communication cradle that is attached to a personal computer. Other methods and systems described below incorporate by reference U.S. Pat. Nos. 4,926,871; 5,235,985; 6,569,097; 6,110,111; and 6,676,605 as if fully disclosed herein.

Figure 7:
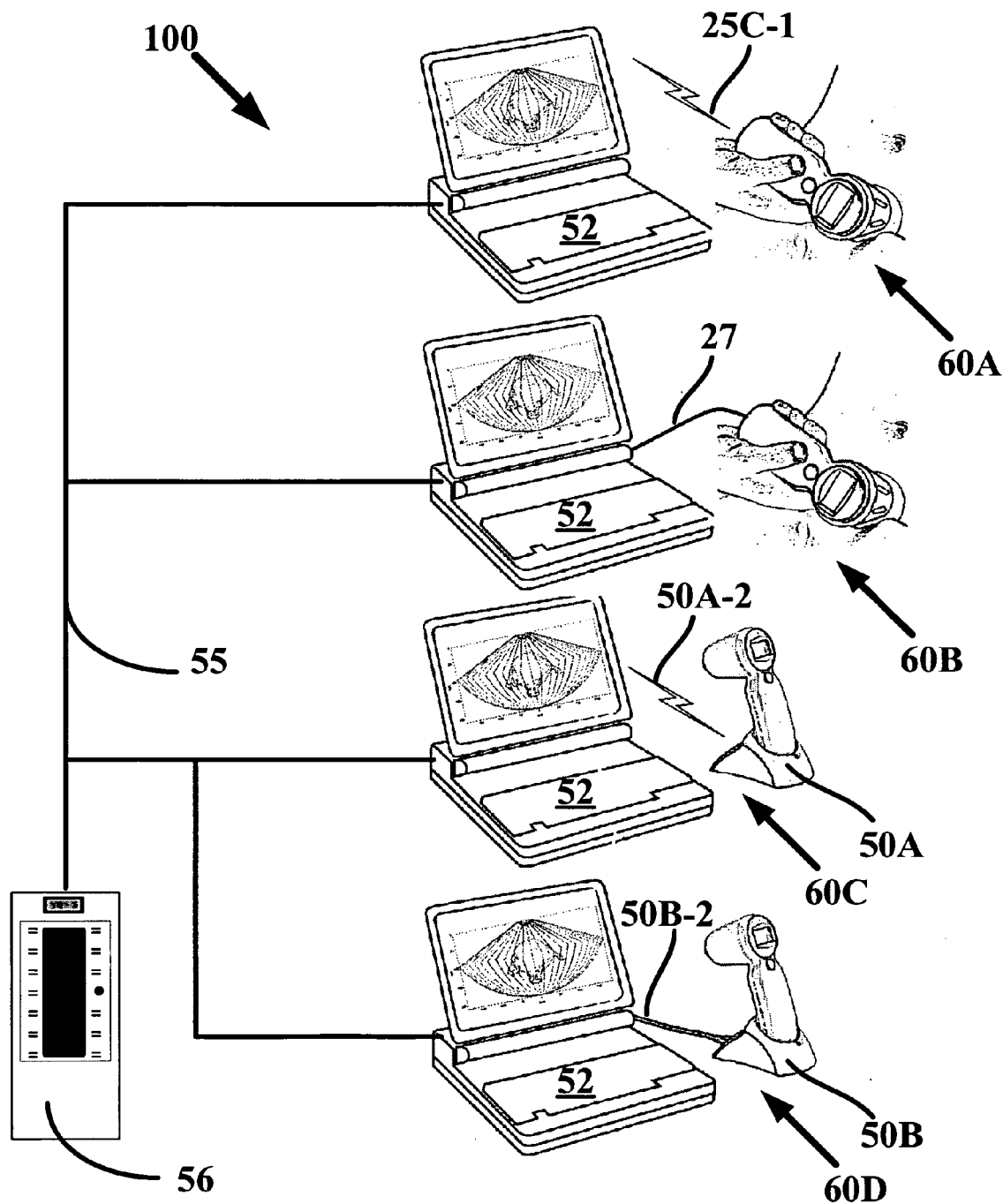
FIG. 7 is a schematic illustration and partial isometric view of a networked ultrasound system 100 in communication with ultrasound imaging systems 60A-D.

Expanding on the protocol described above, and still referring to FIG. 5 the system 60A also includes a personal computing device 52 that is configured to wirelessly exchange information with the transceiver 10C, although other means of information exchange may be employed when the transceiver 10C is used. In operation, the transceiver 10C is applied to a side abdominal region of a patient 68. The transceiver 10B is placed off-center from a centerline 68C of the patient 68 to obtain, for example a trans-abdominal image of a uterine organ in a female patient. The transceiver 10B may contact the patient 68 through a pad 67 that includes an acoustic coupling gel that is placed on the patient 68 substantially left of the umbilicus 68A and centerline 68C. Alternatively, an acoustic coupling gel may be applied to the skin of the patient 68. The pad 67 advantageously minimizes ultrasound attenuation between the patient 68 and the transceiver 10B by maximizing sound conduction from the transceiver 10B into the patient 68. As shown in FIGS. 6 and 7 below, an ultrasound imaging system 60B includes a transceiver 10D that is in wired communication with the computer 52. In this wired embodiment, the transceiver 10D has circuitry that receives and converts the informational content of the scan cone 40 or scan cone 30 to a non-wireless signal that is conveyed in the conduit between the transceiver 10D and computer 52, which may include an electrical, a light, or a sound-based signal.

Wireless signals 25C-1 include echo information that is conveyed to and processed by the image processing algorithm in the personal computer device 52. A scan cone 40 (FIG. 1B) displays an internal organ as partial image 56A on a computer display 54. The image 56A is significantly truncated and off-centered relative to a middle portion of the scan cone 40A due to the positioning of the transceiver 10B.

As shown in FIG. 5, the trans-abdominally acquired image is initially obtained during a targeting phase of the imaging. During the initial targeting, a first freehand position may reveal an organ or ROI 56A that is substantially off-center. The transceiver 10C is operated in a two-dimensional continuous acquisition mode. In the two-dimensional continuous mode, data is continuously acquired and presented as a scan plane image as previously shown and described. The data thus acquired may be viewed on a display device, such as the display 54, coupled to the transceiver 10B while an operator physically translates the transceiver 10C across the abdominal region of the patient. When it is desired to acquire data, the operator may acquire data by depressing the trigger 14 of the transceiver 10C to acquire real-time imaging that is presented to the operator on the transceiver display 14. If the initial location of the transceiver is significantly off-center, as in the case of the freehand first position, results in only a portion of the organ or ROI 56A being visible in the scan plane 40A.

Figure 8:
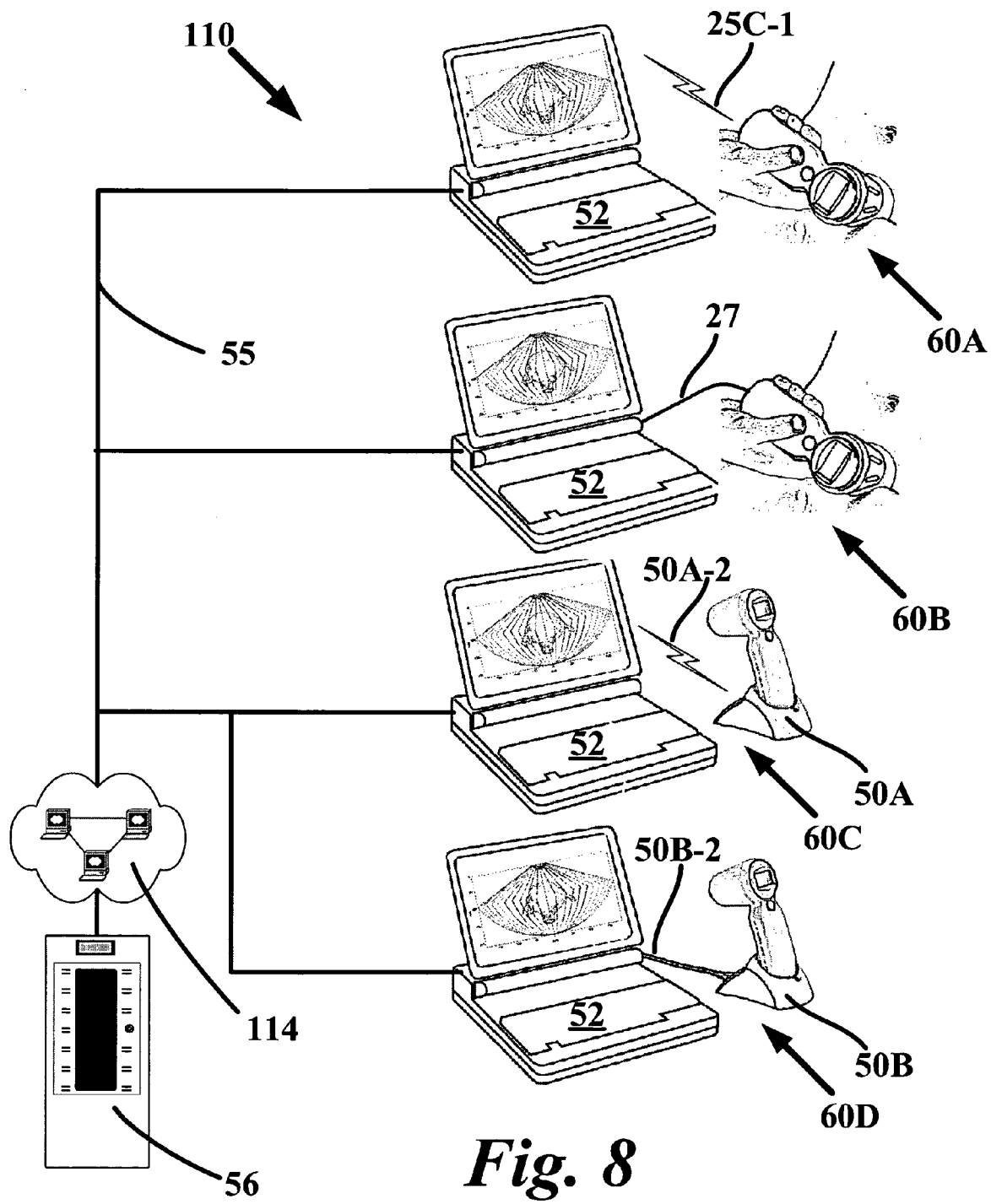
FIG. 8 is a schematic illustration and partial isometric view of an Internet connected ultrasound system 110 in communication with ultrasound imaging systems 60A-D.
Figure 10:
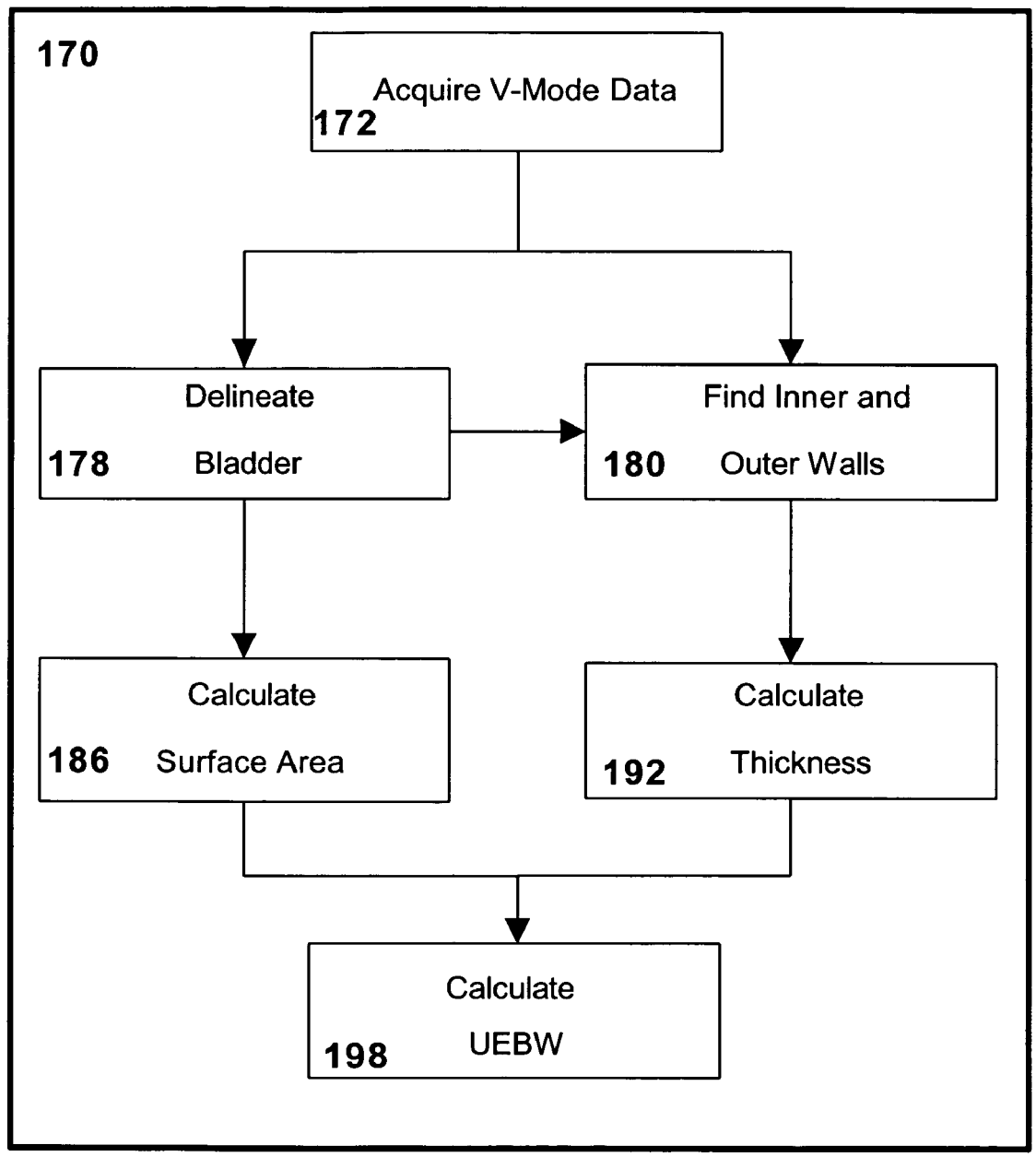
FIG. 10 is an algorithm for the calculation of UEBW from V-mode® ultrasound data.

FIG. 6 depicts images showing the patient 68 being scanned by the transceiver 10C and the data being wirelessly uploaded to a personal computer of a properly targeted ROI in the abdominal area beneath the umbilicus 68A and near umbilicus midline 68C. Here the patient being scanned by the transceiver 10C and the data is wirelessly uploaded to the personal computer 52 occurs when the ROI 56B is properly targeted. The isometric view presents the ultrasound imaging system 60A applied to a center abdominal region of a patient. The transceiver 10C may be translated or moved to a freehand second position that is beneath the umbilicus 68A on the centerline 68C of the patient 68. Wireless signals 25C-2 having information from the transceiver 10C are communicated to the personal computer device 52. An inertial reference unit positioned within the transceiver 10C senses positional changes for the transceiver 10C relative to a reference coordinate system. Information from the inertial reference unit, as described in greater detail below, permits updated real-time scan cone image acquisition, so that a scan cone 40B having a complete image of the organ 56B can be obtained. Still other embodiments are within the scope of the present invention. For example, the transceiver 10C may also be used in the system 60A, as shown in FIG. 10. The transceiver 10A and the support cradle 50A shown in FIG. 3 as well as the transceiver 10A and the support cradle 50B of FIG. 4 may also be used, as shown in FIG. 7 and FIG. 8 below, respectively. Furthermore, the transceivers 10A or 10B may be equipped with an inertial reference system to determine the location coordinates of the transceivers 10A or 10B in relation to the patient 68. The inertial reference systems may employ accelerometers 22 to determine the translational component of the location coordinates and gyroscopes 23 to determine the rotational component of the location coordinates.

FIG. 7 is a schematic illustration and partial isometric view of a network connected ultrasound system 100 in communication with ultrasound imaging systems 60A-D. The system 100 includes one or more personal computer devices 52 that are coupled to a server 56 by a communications system 55. The devices 52 are, in turn, coupled to one or more ultrasound transceivers, for examples the systems 60A-60D. The server 56 may be operable to provide additional processing of ultrasound information, or it may be coupled to still other servers (not shown in FIG. 7) and devices, for examples transceivers 10A or 10B equipped with snap on collars having an inertial reference system that may employ at least one accelerometer 22 to determine the translational component of the location coordinates and at least one gyrosocope 23 to determine the rotational component of the location coordinates.

FIG. 8 is a schematic illustration and partial isometric view of an Internet connected ultrasound system 110 in communication with ultrasound imaging systems 60A-D. The Internet system 110 is coupled or otherwise in communication with the systems 60A-60D through an array of computers 114 in remote signal communication with the server 56. The array of computers 114 may include other computers similar to the computer 52 of systems 60A-D. The system 110 may also be in communication with the transceiver 10A or 10B having inertial reference capability as described above.

Figure 9A:
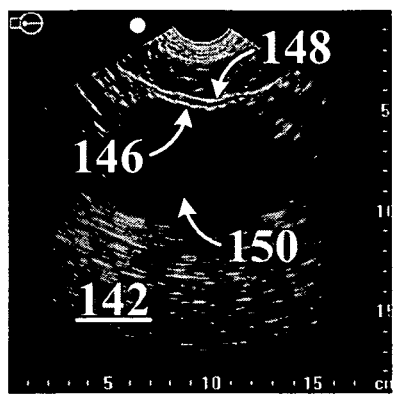
FIG. 9A is a B-mode ultrasound image of a bladder in a transverse section using the either of the transceivers 10A-C with 3.7 MHz pulse frequency from imaging systems 60A-D.

FIG. 9A is a B-mode or two-dimensional ultrasound image of a bladder in a transverse section using one of the transceivers 10A-B of FIG. 1A and FIG. 2, respectively, with 3.7 MHz pulse frequency from imaging systems 60A-D. FIG. 9A shows the ultrasound appearance of a transverse section of a bladder lumen 150 visualized as a dark semi-circular or pumpkin-shaped region within scan plane 142. The bladder lumen 150 presents as a dark region in the center region of scan plane 142 due to the nature of fluids or empty spaces within the bladder lumen being hypoechoic. More solid-like tissue barriers are echoic to incoming or probing ultrasound energy and reflect back the incoming probing ultrasound. The barrier-reflected ultrasound present as bright regions with in the scan cone 142. The echoic barriers outlining the bladder perimeter proximal to the transducer dome 41 cutout is shown as a sub-mucosal 146 layer and sub-serosal layer 148 of the anterior region of the bladder wall.

Figure 9B:
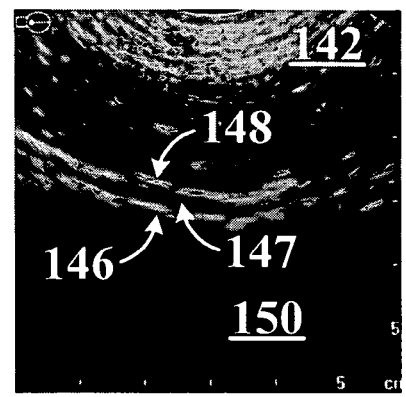
FIG. 9B is a close-up of the image in FIG. 9A showing the anterior bladder wall.

FIG. 9B is a close-up of the image in FIG. 9A showing the anterior bladder wall. The zoomed image results from a series of log-compressed A-mode lines and closely shows the cross-sectional structure of the anterior wall of the bladder 150. A relatively lighter region 147 is shown interposed between the brighter sub-mucosal 146 and sub-serosal layers 146 and 148. The detrusor bladder wall muscle occupies the less bright region 147. Though less bright than layers 146 and 148, the detrusor muscle region 147 is brighter than the bladder lumen 150.

Figure 9C:
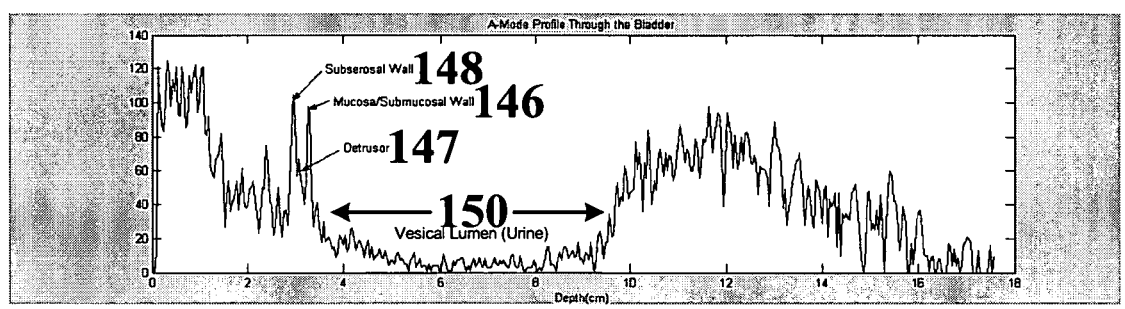
FIG. 9C is a log-compressed A-mode line of one scan line similar to scan line 48 through the bladder and illustrates the relative echogenic as a function of scan line position or depth through the bladder.

FIG. 9C is a log-compressed A-mode line of one scan line similar to scan line 48 through the bladder and illustrates the relative echogenic as a function of scan line position or depth through the bladder. The sub-mucosal layer of the wall, the sub-serosal layer, and the detrusor muscle are visualized in this particular set of zoomed B-mode and the A-mode data. These two layers of the bladder wall are most clearly visible when the ultrasound beam is normally incident to the bladder wall. As the ultrasound incidence deviates from normal, the two layers start appearing as one and may not be reliability detected. While in many data sets these two layers of the bladder walls are clearly visible at normal incidence, there are some cases when the perivesical tissue (such as the peritoneum) impinges on the bladder wall and merges with the subserosal layer. Some samples of such images where the peritoneum merges with the subserosal layer are shown in FIG. 9C.

As shown in FIG. 9C, a significantly resolving histogram is obtained when an ROI is probed with incoming ultrasound that is substantially normal to the organ or ROI. Here cross-sections of structures of FIGS. 9A and 9B are seen with enough fine detail to be distinguished from each other. A one-dimensional histogram plot of ultrasound echo intensity along an A-line scan line similar to scan line 49 of FIG. 1D, scan lines 31A-F, or scan lines 34A-C of FIG. 2 is plotted against the depth of the scan line. The sub-serosal layer 148 is shown being slightly more echogenic than the more distal sub-mucosal layer 146. The sub-serosal layer 148 is approximately 3 cm from the scan head dome 20 and the sub-serosal layer approximately 3.5 cm from the dome 20. The bladder lumen 150 is shown spanning between the anterior located sub-serosal layer 146 to a more posterior depth near 9.5 cm. Compared to the darker bladder lumen 150, the relatively brighter detrusor region 147 is shown interposed between the even brighter sub-mucosal and sub-serosal layers 146 and 148.

FIG. 10 is an algorithm 170 for the calculation of UEBW from V-mode® ultrasound data. The algorithm permits the calculation of UEBW from V-mode® ultrasound data. Bock 178 in the algorithm 178 is to delineate the bladder region. This delineated bladder region is then used to calculate the bladder surface area as shown at block 186. Using the delineated bladder region and the input V-mode® data obtained at block 172, the anterior wall of the bladder is determined. This anterior wall delineation is used to calculate the bladder wall thickness. Finally, the surface area and the thickness measurements are combined to calculate the UEBW, as shown at block 198. Though algorithm 170 is directed to determining wall weight and/or masses of bladders, algorithm 170 may also be directed to non-bladder regions-of-interests, such as a uterus, a heart, a kidney, or tumors of cancerous and/or non-cancerous origins. Non-cancerous tumors may include parasitic infections having a sack like growth.

Figure 11:
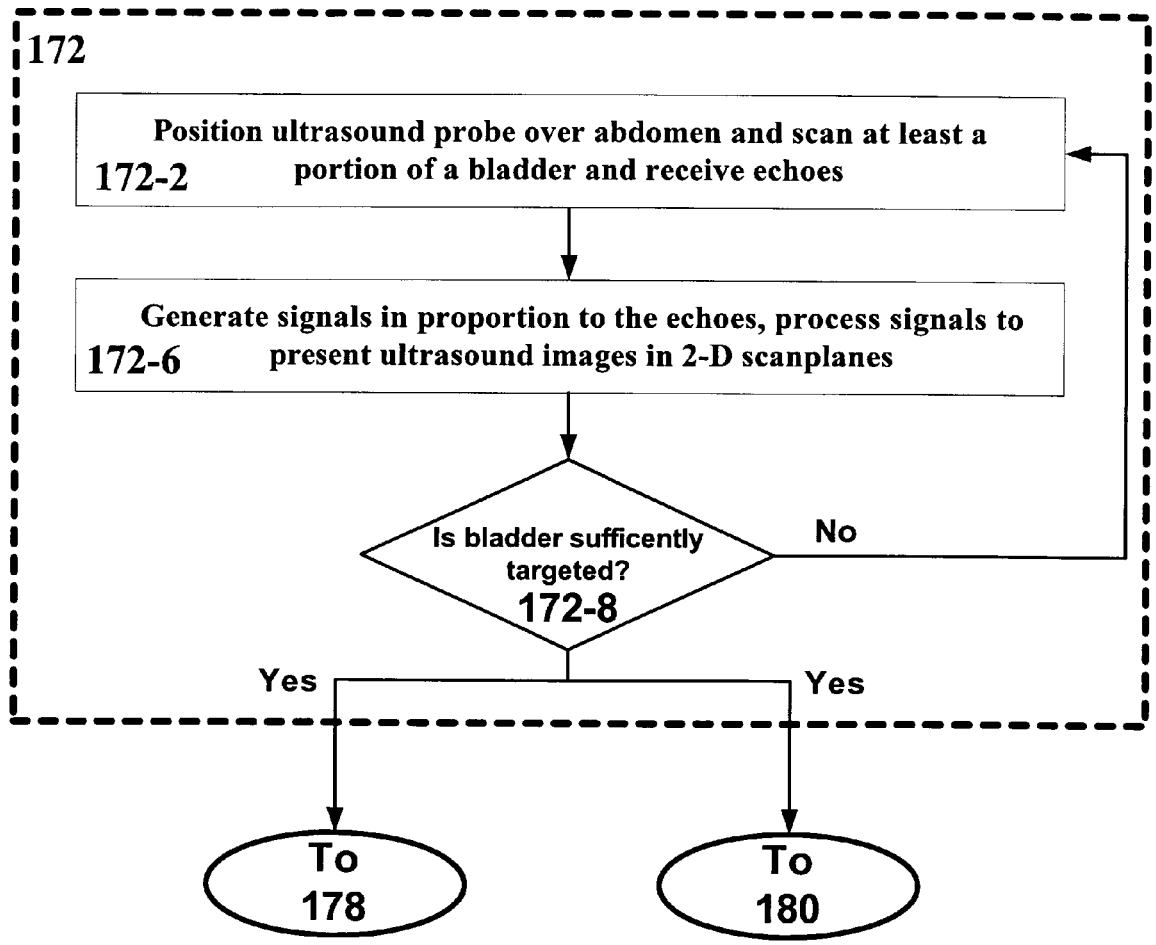
FIG. 11 is an expansion of sub-algorithm 172 of FIG. 10.

FIG. 11 is an expansion of sub-algorithm 172 of FIG. 10. At block 172-2 the ultrasound probe is positioned over an abdomen to ultrasound scan at least a portion of a bladder. Returning echoes from the bladder are received by the transceiver 10A or 10B. Thereafter, at process block 172-6, signals are generated in proportion to the strength of the returning ultrasound echoes. The signals are processed into ultrasound images by image processing algorithms discussed below that are executable by microprocessors located in the computer 52, local server 56, or other servers and computers accessible by the Internet 114. In either case, an image of the bladder is presented for viewing by a user on the computer display 54. Thereafter, at decision diamond 172-8 presents a query "Is bladder sufficiently targeted?". Methods for determining targeting sufficiency is more fully described in U.S. Pat. No. 6,884,217 to McMorrow et al. which is incorporated by reference herein. If the answer is "no", sub-algorithm 172 returns to block 172-2 and proceeds to toward decision diamond 172-8. If the answer is "yes", then sub-algorithm 172 is finished and exits to sub-algorithms 178 and 182 that are subsequently engaged.

Figure 12A:
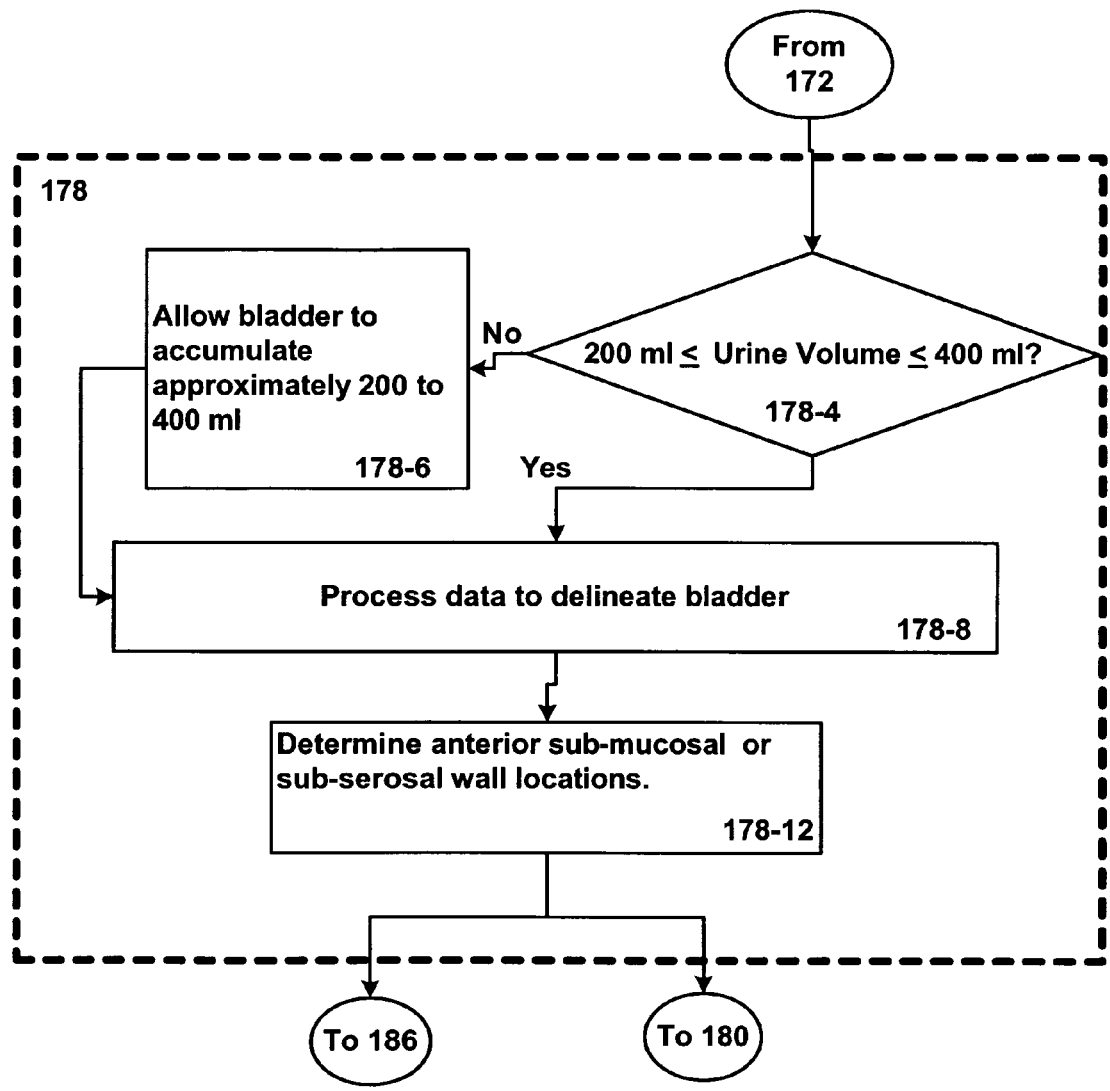
FIG. 12A is an expansion of sub-algorithm 178 of FIG. 10.

FIG. 12A is an expansion of sub-algorithm 178 of FIG. 10. Sub-algorithm 178 begins with entry into decision diamond 178-4 to answer to the query "Is the urine volume between 200 and 400 ml?" expressed in mathematical terms as "200≦urine volume≦400 ml?". If the answer is Yes, then Data is processed at block 178-8 to delineate the bladder. If the answer is No, then at block 178-6 the bladder is allowed to accumulate enough urine to be within 200 and 400 ml. After the urine volume falls within 200 and 400 ml, the anterior submucosal and anterior subserosal wall locations are determined at block 178-12. Thereafter, sub-algorithm 178 exits to process block 186 or 192.

Figure 12B:
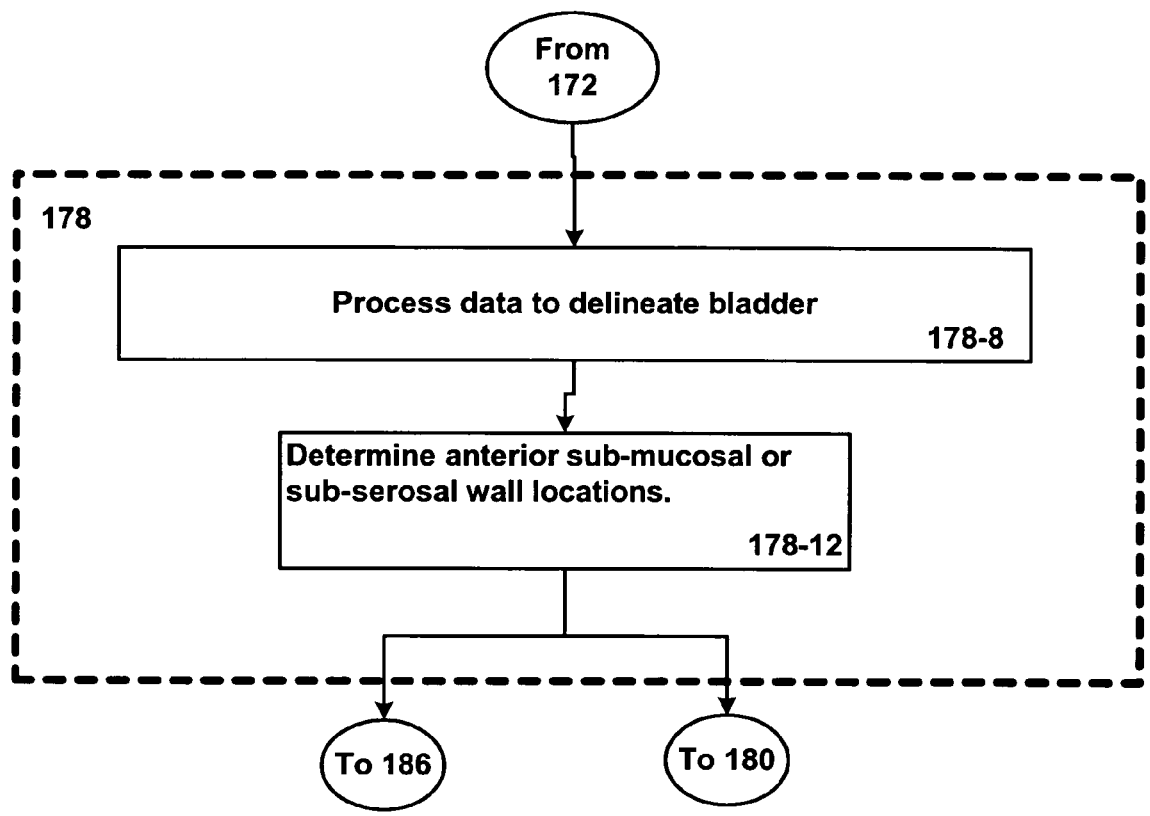
FIG. 12B is an expansion of an alternate embodiment of sub-algorithm 178 of FIG. 10.

FIG. 12B is an expansion of an alternate embodiment of sub-algorithm 178 of FIG. 10. UBEW may be determined at volumes less than 200 ml or greater than 400 ml, though the accuracy may not be optimal compared bladders having between 200 and 400 ml urine. When circumstances do not allow for 200-400 ml to be collected in the bladder, then process block 172 may proceed directly to process block 178-8 wherein the acquired data is processed to delineate the bladder. Thereafter, at process block 178-12, the anterior sub-mucosal and sub-sersosal wall locations are determined. From here, the method continues to process block 186 and 192.

Figure 13:
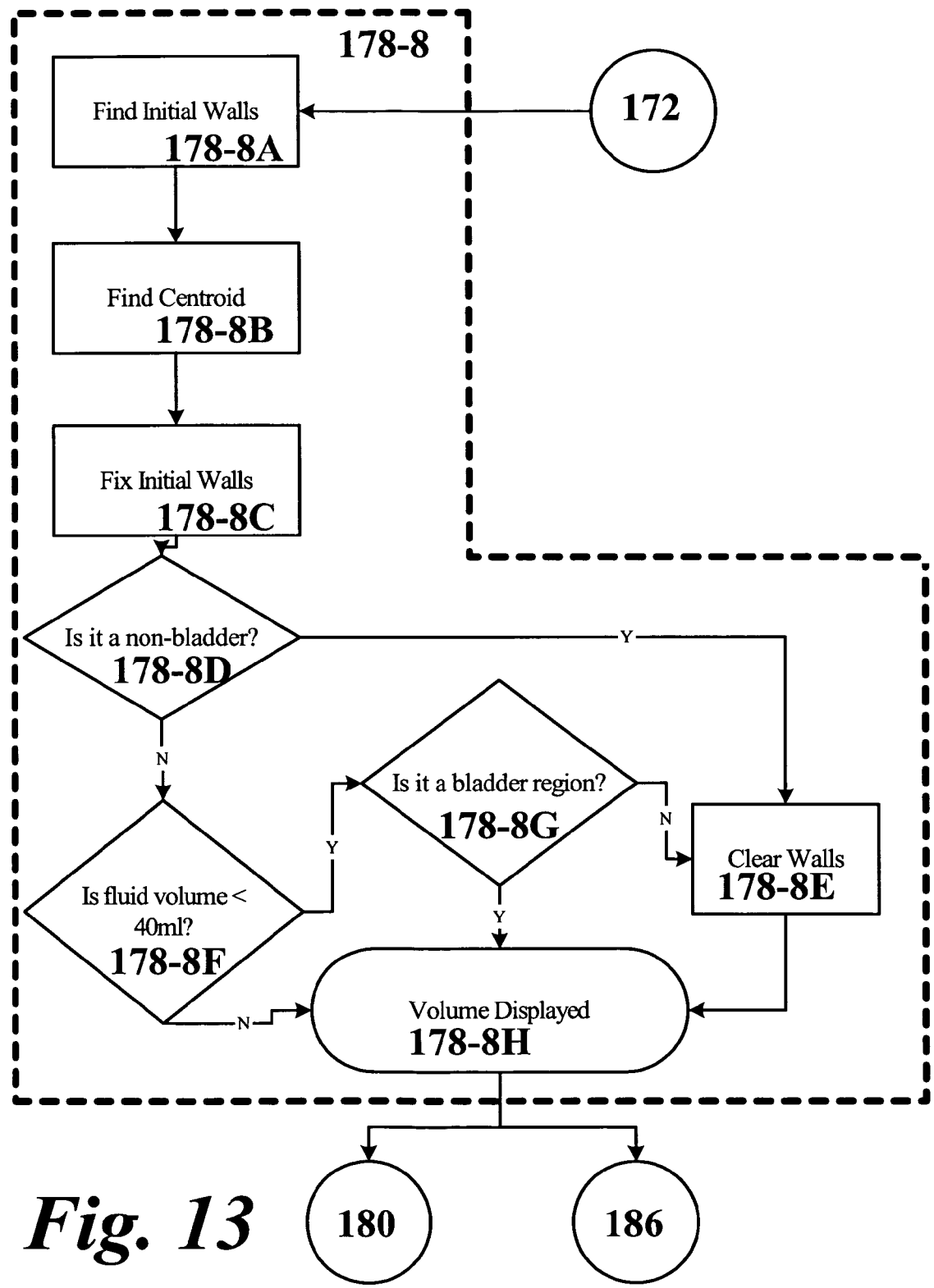
FIG. 13 is an expansion of the process data to delineate bladder sub-algorithm 178-8 of FIGS. 12A and 12B.

FIG. 13 is an expansion of the process data to delineate bladder sub-algorithm 178-8 of FIGS. 12A and 12B. The sub-algorithm 178-8 is comprised of eight process or decision routines and begins after completion of sub-algorithm 172 with the first process block 178-8A referred to as Find Initial Wall. From Find Initial Wall block 178-8A is the next block 178-8B that entitled Find Centroid. Thereafter, block 178-8C is Fixed Initial Walls. After Fix Initial Walls is a decision block 178-8D with a query asking, "Is it a non-bladder?" If the answer is "yes" that the organ is a non-bladder, the next process is Clear Walls block 178-8E. Thereafter, the volume is displayed at block 178-8H and the process 178-8 continues on to sub-process 178-8J. Referring back to decision diamond 178-8D, if the organ is not a non-bladder, that is "no", then another decision 178-8F presents the query "Is volume less than 40 ml?" If the answer is "no" to the decision diamond 178-8F, then the volume is displayed at terminator 178-8H and the algorithm 178-8 proceeds to sub-algorithm 178-8J. If at decision diamond 178-8F the answer is "yes" to the query, "Is volume less than 40 ml?", another decision is presented at diamond 178-8G with the query "Is it a bladder region?" If the answer is "no" then the sub-algorithm 178-8 proceeds to the Clear Walls of block 178-8E and thence to terminator block 178-8H Volume Displayed. If at the decision diamond 178-8G, the answer is "yes" to the query, "Is it a bladder region?" then the volume is displayed at terminator 178-8H and process 178-8 continues on to algorithms 180 and 186. In sub-algorithm 178-8, an interface line is overlaid on the B-mode scan plane image to approximate an initial location for an organ wall, for example, a uterus or a bladder. This initial interface line is used as a seed or initial reference point which is further used as a basis to adjust the determination for the inner and outer wall layers of the organ wall. Furthermore, in this algorithm, the detected region in the scan plane is determined to be or not to be a bladder or a uterus. This occurs specifically when a gender button (not shown) of the transceiver 10A (FIG. 1A) indicates that the scan is for a female. If the regions indeed are found to be a uterus, it is cleared and a zero volume is displayed. For a non-uterus region, such as a bladder, if the volume is very small, then checks are made on the size of a signal characteristic inside the detected region to ensure that it is a bladder and not another tissue. If a region is indeed a bladder region it is computed and displayed on the output.

Figure 14:
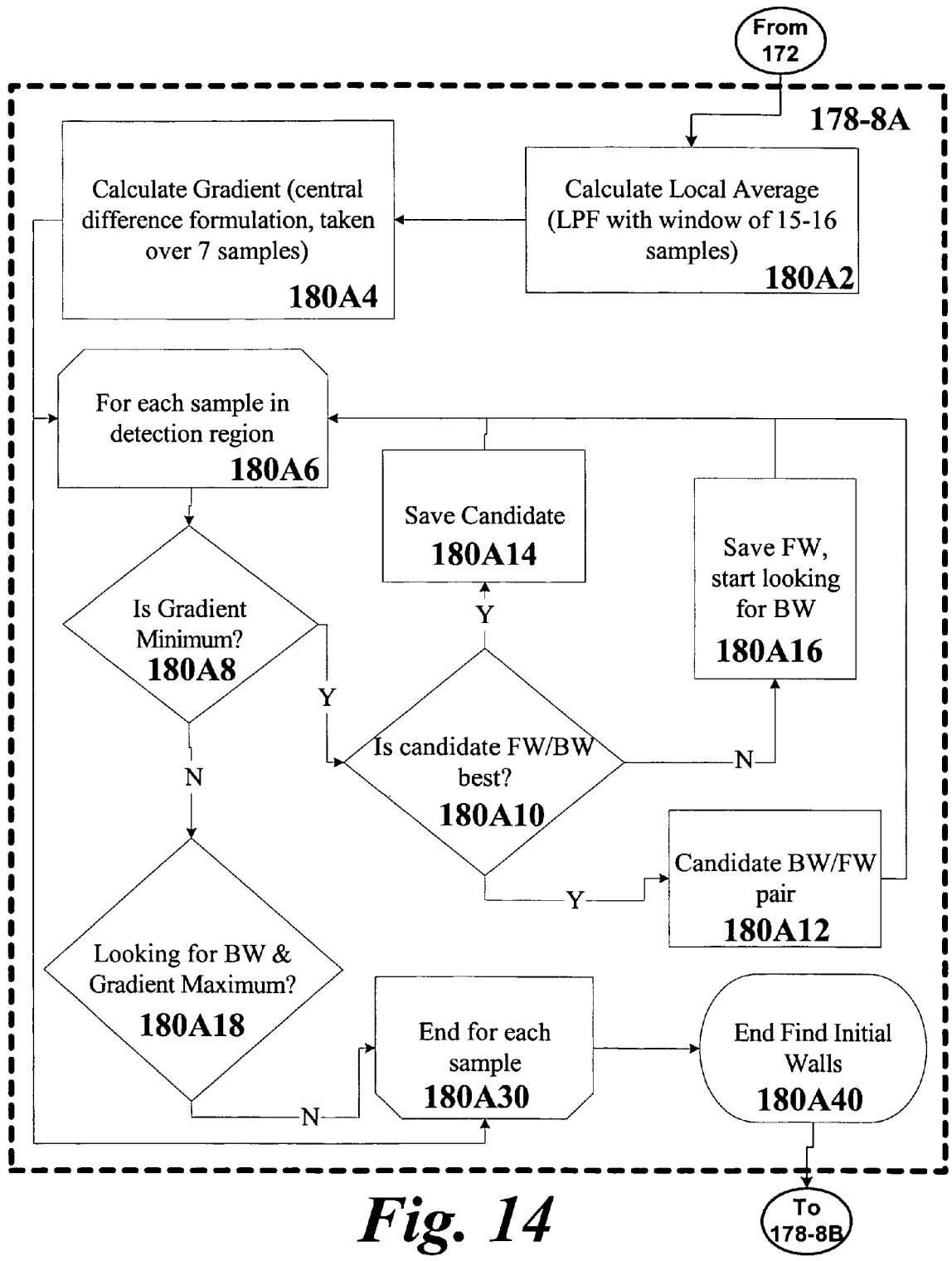
FIG. 14 is an expansion of the Find Initial Walls sub-algorithm 178-8A of FIG. 13.

FIG. 14 is an expansion of the Find Initial Walls sub-algorithm 178-8A of FIG. 13. The sub-algorithm 178-8A is comprised of 11 processes loops, decisions, and terminators. Sub-algorithm 178-8A begins with process 180A2 in which the Local Average is calculated for the 15 to 16 samples that functions as a low pass filter (LPF) to reduce noise in the signal. Other embodiments allow for calculating averages from less than 15 and more than 16 samples. Next is block 180A4 in which the gradient is calculated using a central difference formulation and has taken over seven sample sets. The process at block 180A4 then proceeds to a beginning loop limit 180A6. In block 180A6, each sample is examined in a detection region. Thereafter, at decision diamond 180A8, the query is, "Is gradient minimum?" If the answer is "no" then, another query is presented at decision diamond 180A18, the query being, "Looking for BW and gradient maximum?" BW refers to for back wall. If the answer to the query in block 180A18 is "no" then, the end of the loop limit is proceeded to at block 180A30. Thereafter, from the end of the loop limit at 180A30, the terminator end find initial walls is reached at block 180A40. Returning now to the decision diamond 180A8, if the answer to the query, "Is gradient minimum?" "yes" then another query is presented in decision diamond 180A10. The query in 180A10 is "Is candidate FW/BW best?" FW is refers to front wall and BW refers to back wall. If the answer to the query in block 180A10 is "no", then the process 180A62 is used in which the front wall data is saved and another back wall is looked for. If the query to in 180A10 is "yes" then the process is Save Candidate occurs at block 180A14. Thereafter, the process returns to beginning loop 180A6 to resume. Returning to the decision diamond 180A10, should the answer be "yes" to the query, "Is candidate FW/BW best, then the process proceeds to block 180A12 in which the candidate is assigned as a pair for back wall/front wall." Thereafter from block 180A12, the algorithm 186A returns to the beginning loop 180A6 and then the process will then terminate at end of each sample at end loop 180A30 and thence to terminator 180A40 for end find initial walls sub-algorithm and proceed to sub-algorithm 178-8B. Sub-algorithm 178-8A attempts to find the best front wall and back wall pair for the inner and outer wall layer plotting points. The best front wall and back wall pair in each scan line is defined as the front wall and back wall pair for which the difference in the back wall gradient and front wall gradient sometimes referred to as the tissue delta, is the maximum and the smallest local average between the front wall and back wall pair is the minimum for the pixel values.

Figure 15:
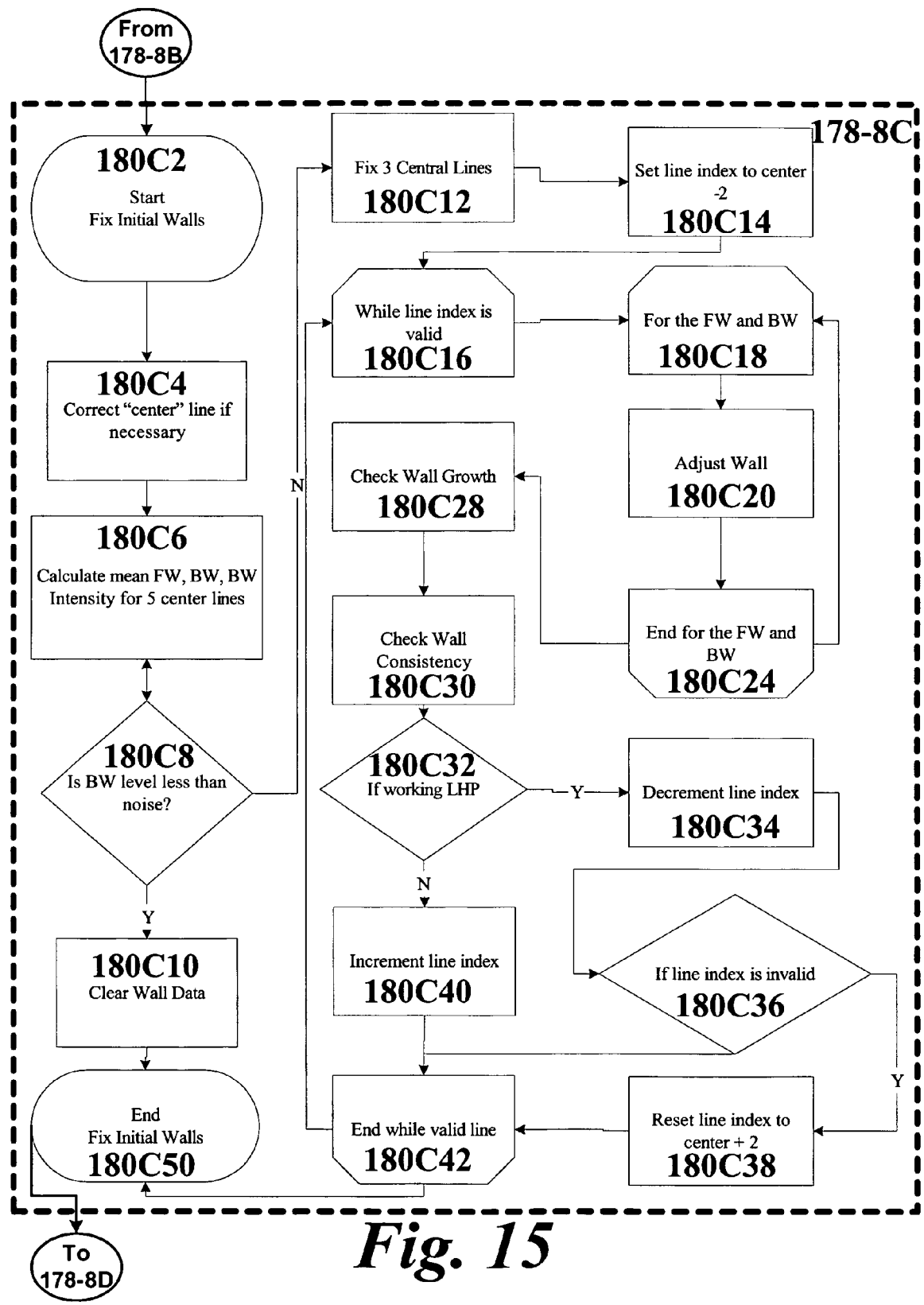
FIG. 15 is an expansion of the Fix Initial Walls sub-algorithm 178-8C of FIG. 13.

FIG. 15 is an expansion of the Fix Initial Walls sub-algorithm 178-8C of FIG. 13. Sub-algorithm 178-8C is comprised of several processes decision diamonds and loops. Sub-algorithm 178-8C operates on a scan plane by scan plane basis where the first scan plane to be processed is one that is closest to the central aid of the initial walls and then the remaining scan planes are processed moving in either direction of that initial scan plane. Sub-algorithm 178-8C begins at block 180C2 referred to as Start Fix Initial Walls. The first process is at block 180C4 in which the center line is corrected if necessary. The center line is defined as the line on that scan plane with the maximum gradient difference between the front wall and the back wall. The correction of the front wall and the back wall location at any line is carried out by a match filtering like step where the best, location within a search limit is defined as the one for which the difference between points immediately outside the bladder and points immediately inside the bladder is maximum. Of course, this applies to any organ other than the bladder, as the bladder is used here as an example of a particular embodiment. Thereafter, at block 180C6, the front wall and back wall means are calculated for five central lines. The pixel main intensity is computed and if this intensity is less than expected from the noise at that depth, the lines are cleared and the algorithm proceeds to the next plane as shown in decision diamond 180C8 to the query, "Is BW level less than noise?" where BW means the back wall (or posterior wall) of the bladder. If the answer is "yes" to this query, at block 180C10, the process Clear Wall Data is initiated and from that proceeds to terminator 180C50 End Fix Initial Walls. Returning to the decision diamond 180C8, if the answer is "no" to the query, "Is BW level less than noise?" then the sub-algorithm 180C proceeds to the process at block 180C12 described as Fix 3 Central Lines. From this point through the end of sub-algorithm 180C, the purpose is first correct the lines to the left of the central lines, called the left half plane (LHP) until either the edge of the bladder or the edge of the ultrasound cone is found. After the algorithm corrects the LHP, it proceeds to correct the lines to the right of the central lines, called the right half plane. Because the same steps are used for all lines, regardless of their position to the left of center or to the right of center, the process blocks 180C16 through 180C42 are used for both the LHP and once for the right half plane. The "line index" of process 180C14 indicates an identifier for the current line that is processed. The line index is set to 2 indices less than the center line to start processing the LHP. The looping procedure started in block 180C16 continues looping while the line index is a valid index (i.e. it corresponds to a scan line). Sub-loop 180C18 is started with the intent of adjusting the initial wall locations, sub-process 180C20, to their correct location if any correction is necessary. This loop, terminated at process 180C24, completes two iterations. The first iteration uses sub-process 180C20 to correct the front wall of the bladder on the current line and the second iteration to correct the back wall of the bladder, although the ordering of which wall is corrected first can be interchanged. Once the wall locations have been corrected of the current line have been corrected, sub-algorithm 180C proceeds to sub-process 180C28, "Check Wall Growth". This sub-process ensures that the length of the scan line that intersects the bladder in the current line does not grow significantly with respect to the previous line that has already been corrected. In the preferred embodiment, the length of the scan line intersecting the bladder is constrained to be less than 1.125 times longer than in the previous line. If the loop bounded by sub-processes 180C16 and 180C42 is being applied to the LHP, then the previous line is one index number greater than the current line index. Otherwise, the previous line index is one index number less than the current index. After completing sub-process 180C28, the sub-process 180C30 "Check Wall Consistency" verifies that the portion of the current scan line that intersects the bladder overlaps the portion of the previous scan line that intersects the bladder. After completing sub-process 180C30, decision 180C32 queries "If working LHP?" (i.e. the loop bounded by terminators 180C16 and 180C42 is being applied to the lines left of center). If the answer to the query is yes, then the sub-process 180C34 "Decrement line index" decreases the line index by one index number. Decision 180C36 queries "If line index is invalid". The loop bounded by terminators 180C16 and 180C42 is applied to the next, and now current, scan line. If the decremented line index corresponds to an invalid value, the edge of the LHP has been reached. Sub-process 180C38 is called to reset the line index to the first line to the right of center that has not been adjusted. The loop bounded by terminators 180C16 and 180C42 will now be applied to the right half plane (RHP). Returning to decision 180C32, if the answer to the query is "No", sub-process 180C40 "Increment line index" results with the line index being increased by one index number. Loop terminator 180C42 cause the loop to return to 180C16 as long as the line index corresponds to an actual scan line. As soon as that condition is violated, the loop terminator will cause sub-algorithm 178-8C to proceed to the terminator 180C50, "End Fix Initial Walls" and proceed to sub-algorithm 178-8D.

Figure 16:
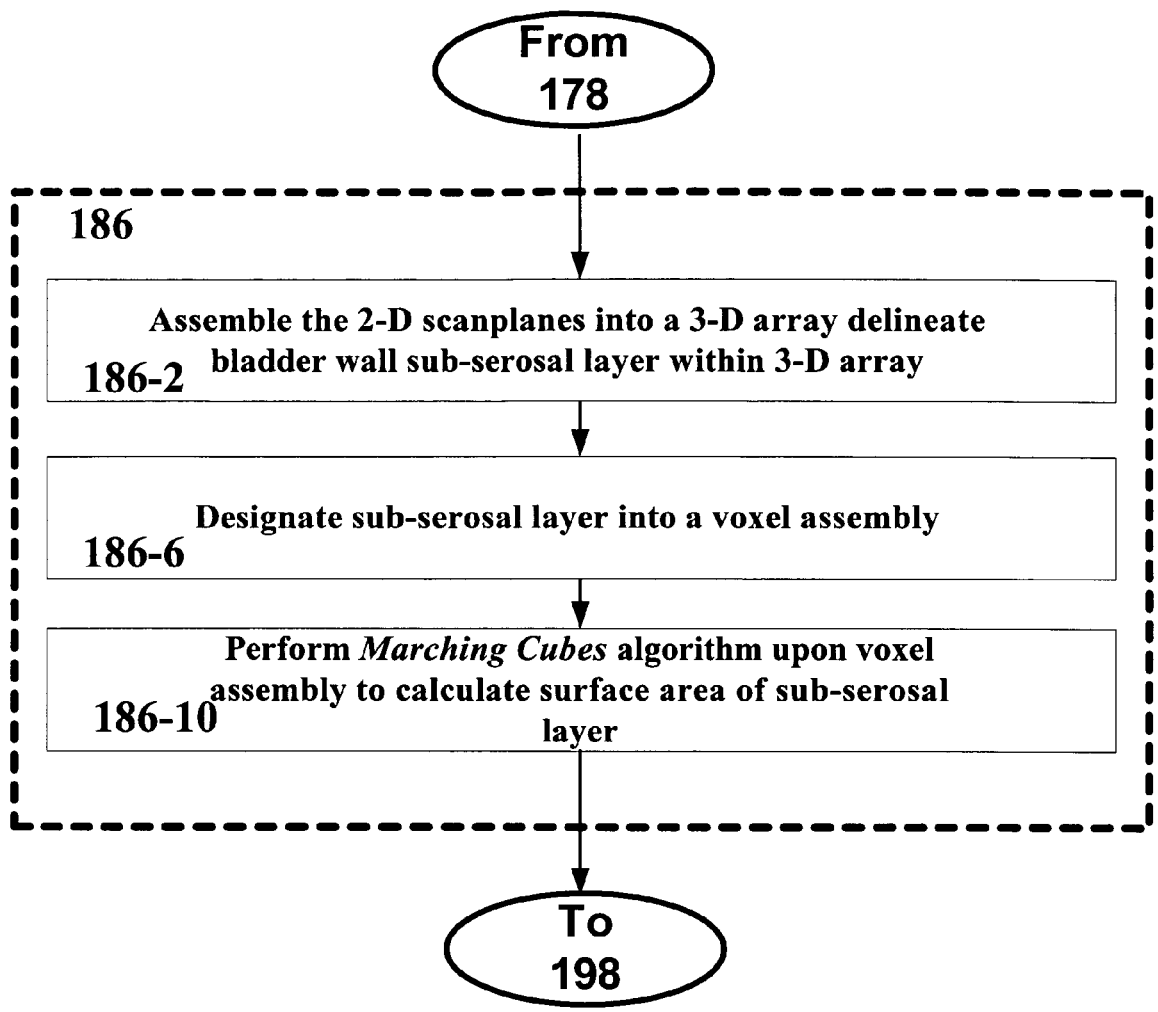
FIG. 16 is an expansion of surface area sub-algorithm 186 of FIG. 10 for sub-serosal layer 148.

FIG. 16 is an expansion of surface area sub-algorithm 186 of FIG. 10. Once the bladder is delineated at sub-algorithm 178, the process continues to block 186-2 wherein the 2-D scan planes are assembled into a 3-D scan cone such as the scan cone 40 of FIG. 1B or scan cone 30 of FIG. 2 and the sub-serosal layer within the 3-D array. When the 3-D scan cone is comprised of scan planes substantially similar to scan plane 42 where the scan lines 48 are confined within a given scan plane 42, the 3-D array may include scan planes assembled into a rotational array, a wedge array, and a translational array. Alternatively, the, the 3-D scan cone, in the form of the scan cone 30 of FIG. 2, is made of a randomly distributed assembly of 3-D distributed scan lines that are not confined to be within any given scan plane. Then, at process block 186-6, the sub-serosal layer is partitioned into a triangular assembly. Thereafter, the surface area of the sub-serosal layer is calculated using a Marching Cubes or other appropriate algorithm at process block 186-10. Knowing the surface area now permits calculation of organ or bladder mass in view of thickness determinations, and organ wall density as described below.

Figure 17:
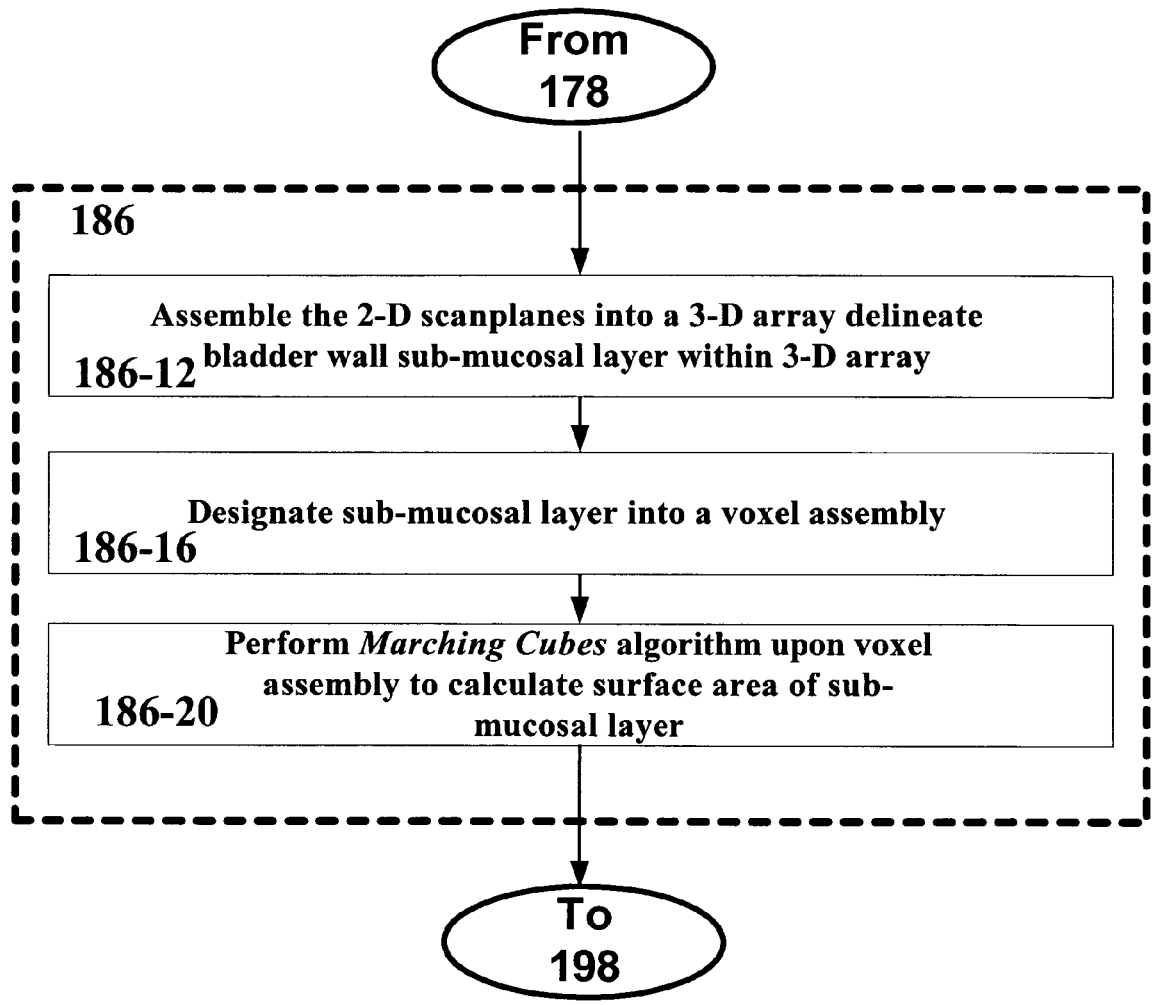
FIG. 17 is an expansion of calculate surface area sub-algorithm 186 of FIG. 10 for sub-mucosal layer 146.

FIG. 17 is an expansion of the calculate surface area sub-algorithm 186 of FIG. 10 for sub-mucosal layer 146. Once the bladder is delineated at sub-algorithm 178 and the sub-serosal layer 148 location approximated, the process 186 begins with block 186-12 wherein the 2-D scan planes are assembled into a 3-D scan cone similar to scan cone 40 or scan cone 30 and the sub-mucosal layer within the 3-D distributed scan lines that are not confined to be within any given scan plane. Then, at process block 186-16, the sub-mucosal layer is partitioned into a triangular assembly. Thereafter, the surface area of the sub-mucosal layer is calculated using a Marching Cubes or other appropriate algorithm at process block 186-20. Knowing the surface area now permits calculation of organ or bladder mass in view of thickness determinations, and organ wall density as described below.

Figure 18:
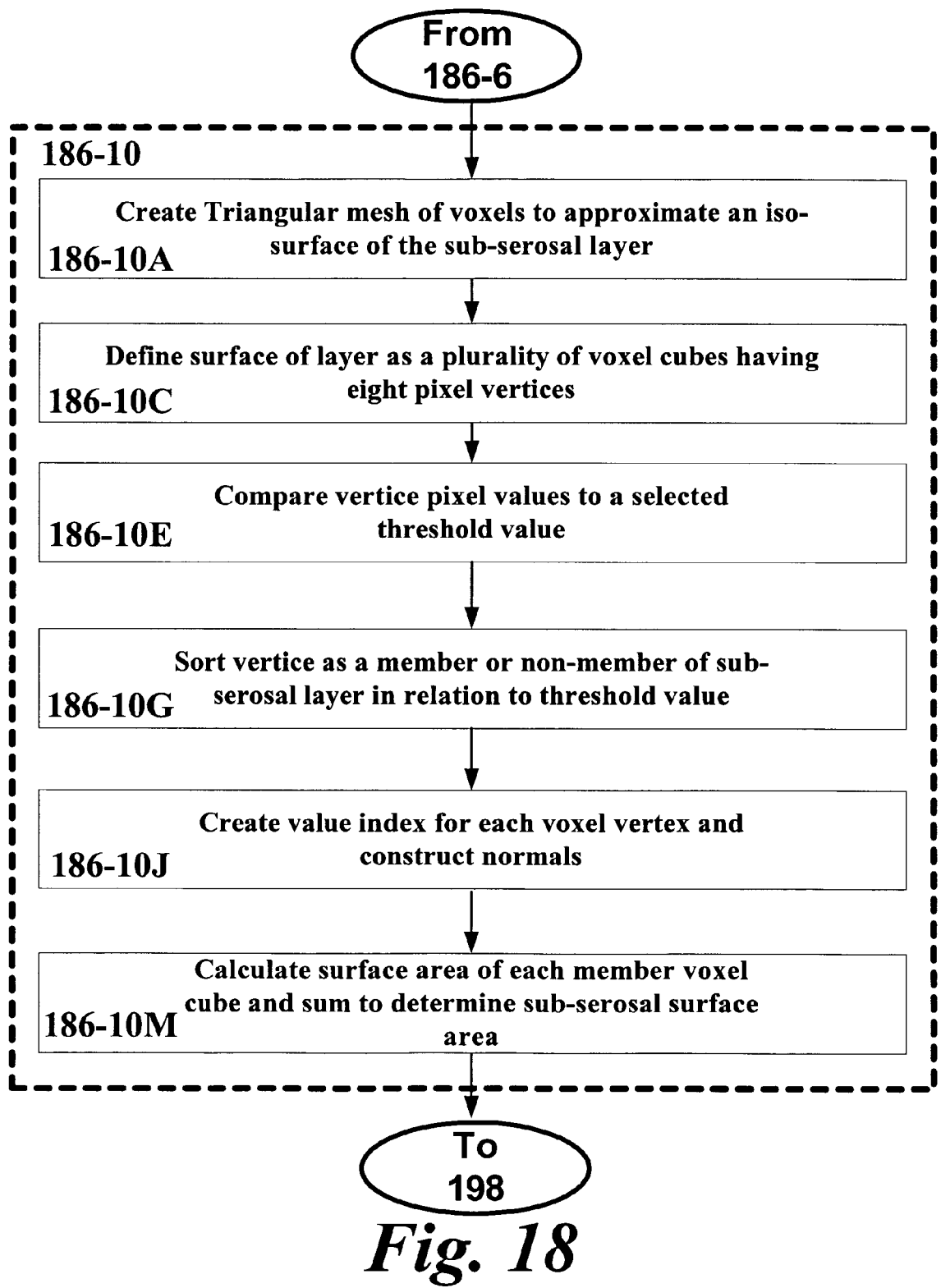
FIG. 18 is an expansion of the sub-algorithm 186-10 of FIG. 16 for sub-serosal layer 148.

FIG. 18 is an expansion of the sub-algorithm 186-10 of FIG. 16 for sub-serosal layer 148. The algorithm 186-10 begins with block 186-10A by creating a triangular mesh of voxels or pixel volume elements defined as an iso-surface or a provisional working representation of the sub-serosal layer 148. Thereafter, at block 186-10C, the iso-surface layer is defined as a plurality of voxel cubes having eight pixel vertices. Thereafter, at block 186-10E, the vertices of the pixel values are compared with a selected threshold voxel or pixel intensity value for the purposes of sorting or classifying voxels as being part of the iso-surface or provisional working representation of the sub-serosal layer 148. How the voxels are sorted is described by block 186-10G. The voxels are defined as being a member or non-member of the iso-surface of the sub-serosal layer 148. A voxel member is defined to be a member if the voxel member has a brightness intensity greater than the threshold value, and a non-member if the voxel has a brightness intensity equal to or less than the threshold value. After sorting and classifying voxels, at block 186-10J, a vertex index value is defined and normals are constructed to the voxels. Thereafter, at block 186-10M, the voxels that are members of the iso-surface are calculated and summed to obtain an accumulated surface area for the sub-serosal layer 148. The algorithm then continues to sub-algorithm 198.

Figure 19:
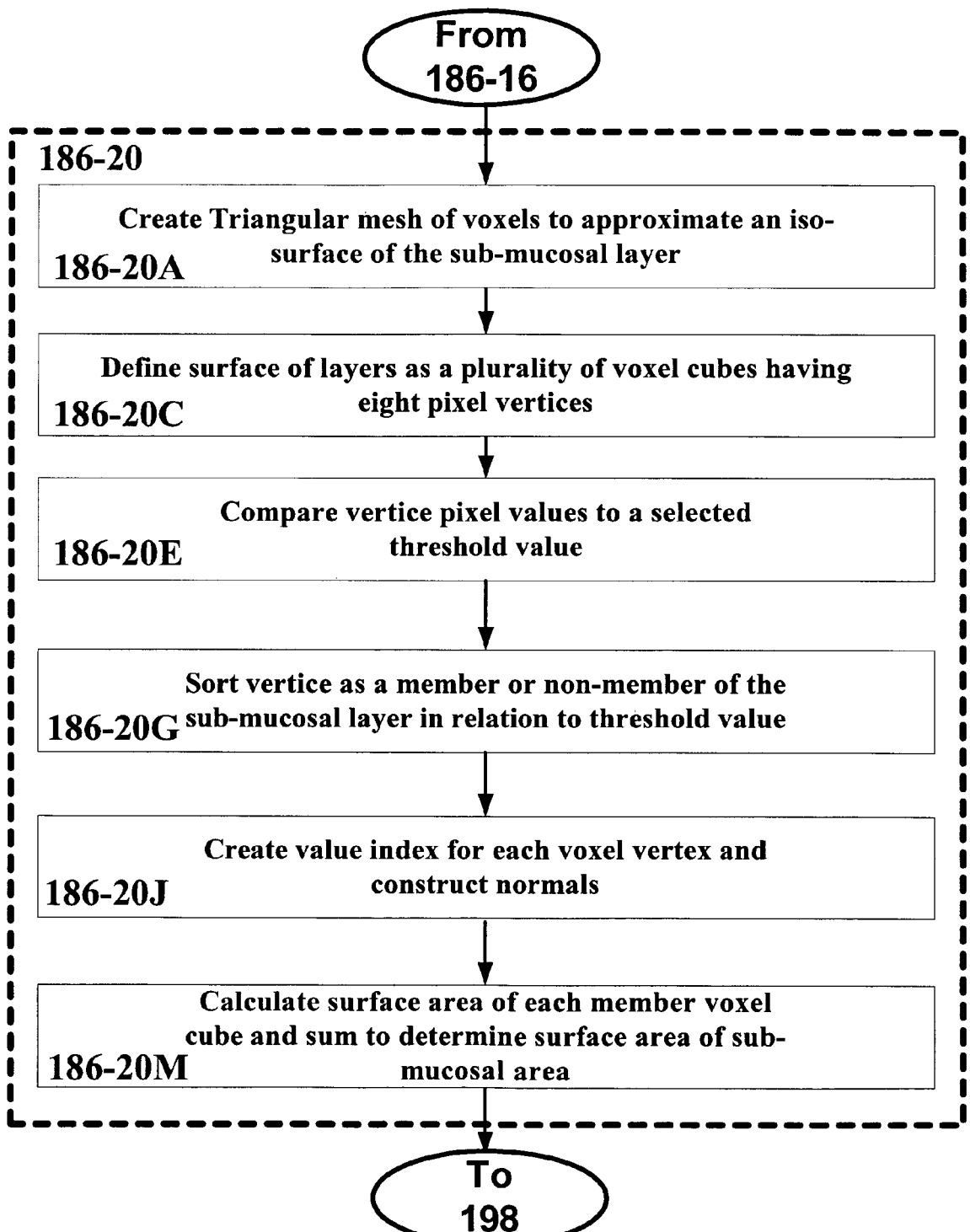
FIG. 19 is an expansion of the sub-algorithm 186-20 of FIG. 17 for sub-serosal layer 146.

FIG. 19 is an expansion of the sub-algorithm 186-20 of FIG. 16 for sub-mucosal layer 146. The algorithm 186-20 begins with block 186-20A by creating a triangular mesh of voxels or pixel volume elements defined as an iso-surface or a provisional working representation of the sub-serosal layer 148. Thereafter, at block 186-20C, the iso-surface layer is defined as a plurality of voxel cubes having eight pixel vertices. Thereafter, at block 186-20E, the vertice pixel values are compared with a selected threshold voxel or pixel intensity value for the purposes of sorting or classifying voxels as being part of the iso-surface or provisional working representation of the sub-serosal layer 148. How the voxels are sorted is described by block 186-20G. The voxels are defined as being a member or non-member of the iso-surface of the sub-serosal layer 148. A voxel member is defined to be a member if the voxel member has a brightness intensity greater than the threshold value, and a non-member if the voxel has a brightness intensity equal to or less than the threshold value. After sorting and classifying voxels, at block 186-20J, a vertex index value is defined and normals are constructed to the voxels. Thereafter, at block 186-20M, the voxels that are members of the iso-surface are calculated and summed to obtain an accumulated surface area for the sub-serosal layer 148. The algorithm then continues to sub-algorithm 198.

Figure 20:
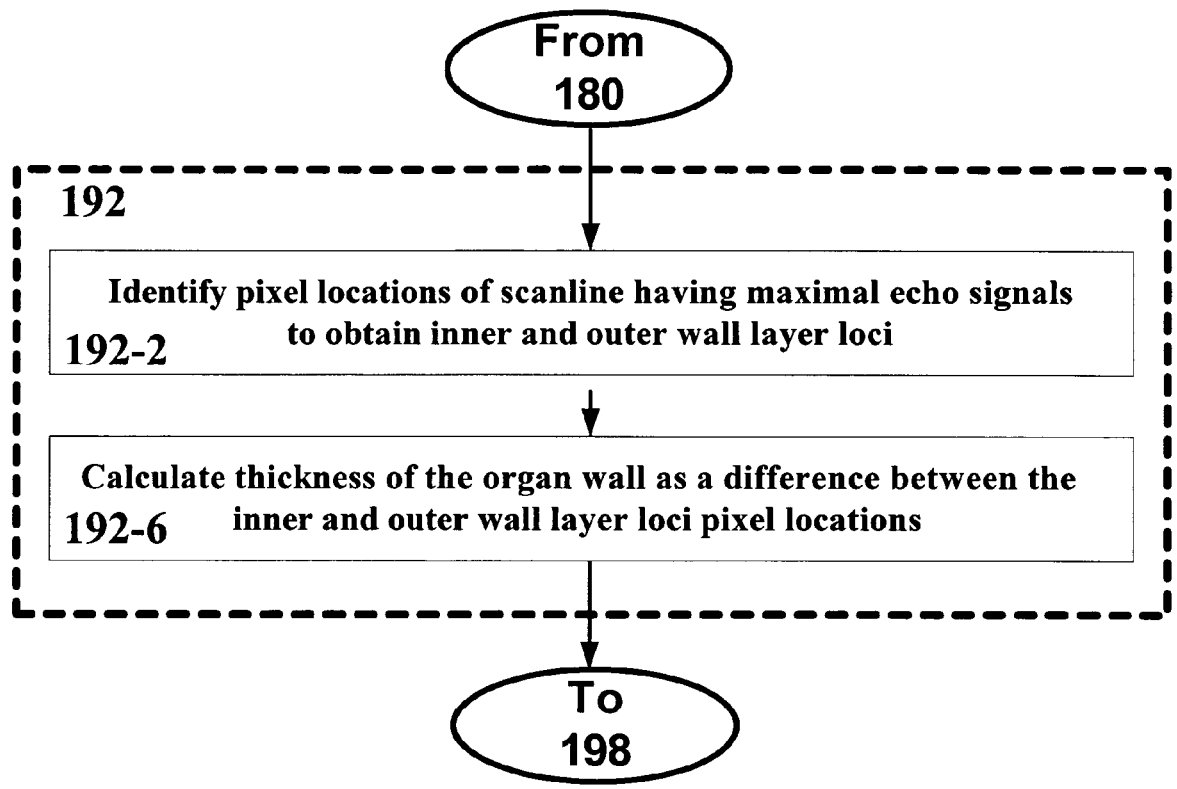
FIG. 20 is an expansion of calculate thickness sub-algorithm 192 of FIG. 10.

FIG. 20 is an expansion of calculate thickness sub-algorithm 192 of FIG. 10. Once the inner (sub-mucosal) and the outer (sub-serosal) layers of the anterior bladder muscle have been delineated, the thickness calculation involves determining the distance between the two surfaces. From block 180, process 192 begins with block 192-2 where the pixels having maximal echo signals are identified to obtain inner and outer wall layer loci. Thereafter, at block 192-6, the thickness of the organ wall is calculated as a difference between the inner and outer wall layer loci pixel locations. The average distance between the inner and outer wall loci are determined on all scan lines approximately normal to the bladder surface. The distance is reported as output and also used for the bladder weight calculation. The rendered bladder wall on the output images shows this average thickness plotted along the two leading edges of the bladder muscle. From here, process algorithm 192 exits to algorithm 198.

Figure 21:
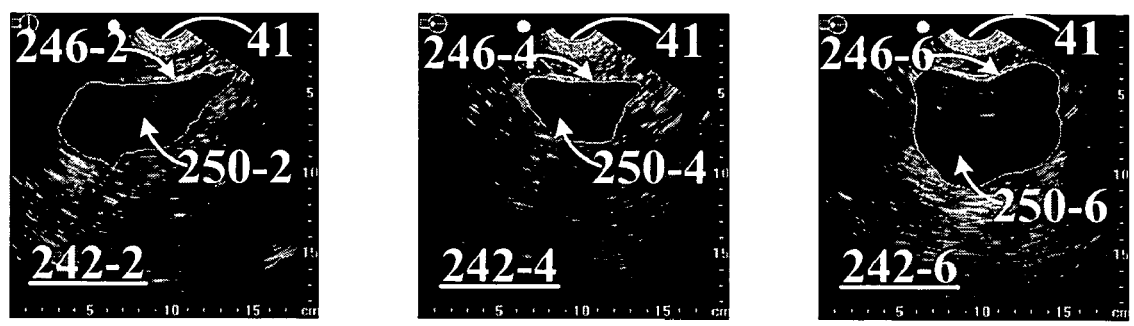
FIG. 21 is a set of three samples of bladder lumen delineations.

FIG. 21 shows sample delineations of the bladder in scan planes 242-2, 4, and 6 respectively. Here the perimeter of the bladder lumen 250-2, 4, and 6 is outlined by sub-mucosal layers 246-2, 4, and 6 using the Find Initial Walls sub-algorithm 180A as previously described. The outlining approximates the general location of the sub-mucosal layers 246-2, 4, and 6 for the purposes of delineating the perimeter of the hypo-echoic bladder lumen 250-2, 4, and 6 to provide a basis to estimate urine volume. The urine volume is estimated to assess whether or not the bladder contains between 200 and 400 ml so that more exacting positioning of the sub-mucosal and sub-serosal layers may be determined by sub-algorithms 178-12, 186, 186-10, and 182-20. Brighter regions are visible anterior to the sub-mucosal layers 246-2, 4, and 6 and towards the dome cutout 41. Regions posterior to sub-mucosal layers 246-2, 4, and 6 are brighter than bladder lumen 250-2, 4, and 6 due to the more echogenic nature of the posterior tissues.

Once the inner surface or of the bladder wall or sub-serosal has been delineated on a set of data planes, the computer graphics algorithm known as the Marching Cubes algorithm, or other appropriate algorithm, may be used to calculate the 3D surface area of the bladder. The Marching Cubes algorithm creates a triangulated three-dimensional surface that is rendered by a computer graphics engine, for example, the VTK Library available from Kitware, Inc., Clifton Park, USA. Pixel intensity values of the triangle vertices dictate whether or not a given pixel constitutes a member of a given wall layer. For example, pixel values below a selected threshold value define a pixel location that is not a pixel member of a surface layer, and pixel values above a threshold value are defined as a surface layer member. Once the triangulated surface is available, calculating the surface area of that 3D surface is achieved by summing up the areas of all the triangles constituting the 3D surface.

Using the delineated bladder surface as a starting point, the anterior wall of the bladder muscle is then determined to enable thickness calculation. For bladder wall finding, the following model is used. When the ultrasound beam is normally incident to the bladder surface, the bladder wall appears as two bright regions representing the sub-mucosal plus mucosal layer and the subserosal layer, separated by a dark region representing the detrusor muscle as shown in FIG. 9C. Thus, first the angle of incidence of a scan line to the bladder surface is determined and then on all scan lines approximately normal to the bladder surface, two bright peaks immediately anterior to the vesicle lumen are located automatically and are labeled as the inner and the outer walls of the bladder muscle.

Figure 22:
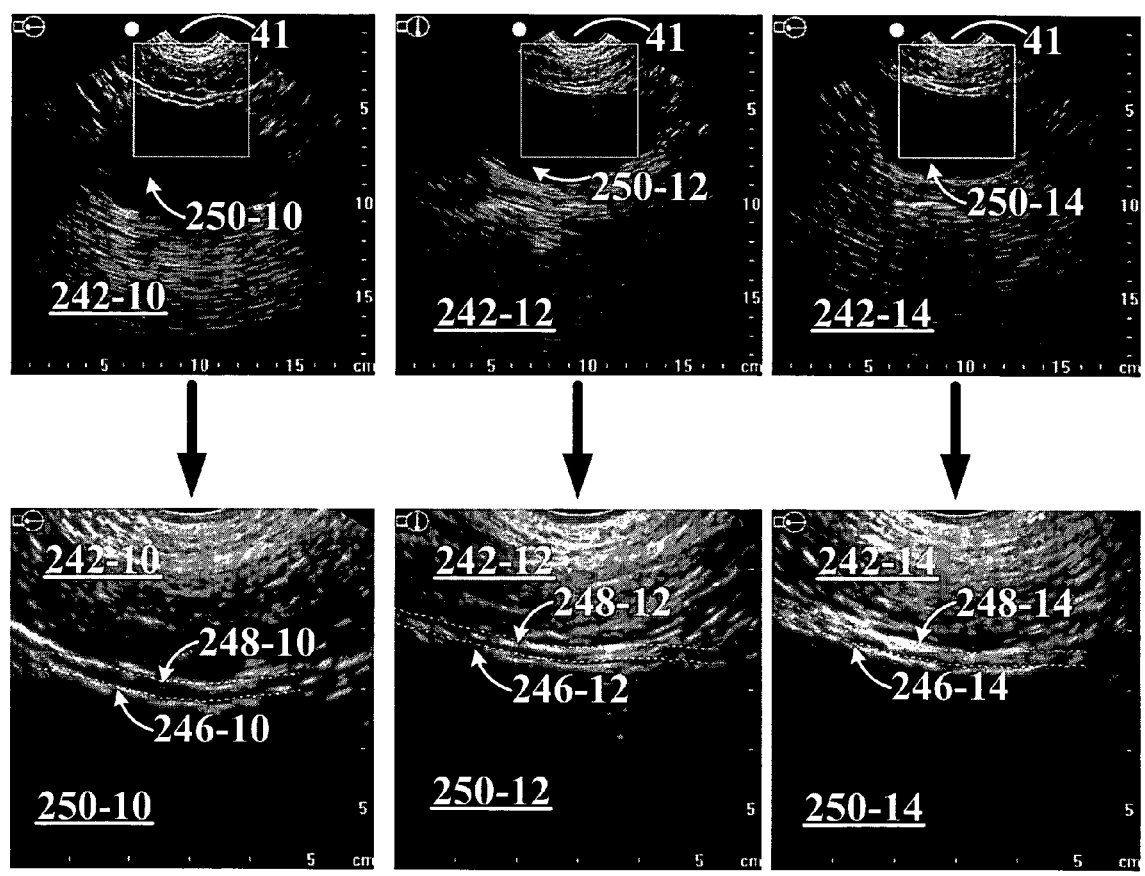
FIG. 22 are a first set of normal and magnified saggital images visualized by the ultrasound transceivers 10A-B.

FIG. 22 are a first set of normal and magnified saggital images visualized by the ultrasound transceivers 10A-B. FIG. 22 illustrates a sample of bladder wall delineations of the anterior bladder adjacent to bladder lumens 250-10, 12, and 14 of the bladder in scan planes 242-10, 12, and 14 respectively. The upper panel of three images is near normal view and shows the full images. The bottom three are magnified or zoomed images of the solid-line highlighted square inset. The sub-mucosal layers 246-10, 12, and 14 and sub-serosal layers 248-10, 12, and 14 of the bladder wall is depicted in dashed lines overlaid in the magnified images. Once the inner (sub-mucosal) and the outer (sub-serosal) layers of the anterior bladder muscle have been delineated, the thickness calculation involves determining the distance between the two surfaces. The average distance between the inner and outer wall are determined on all scan lines approximately normal to the bladder surface—this distance is reported as output and also used for the bladder weight calculation. The rendered bladder wall on the output images shows this average thickness plotted along the two leading edges of the bladder muscle. In cases where the perivesical tissue merges with the subserosal layer of the bladder, the ultrasound reflection from the perivesical tissue merges with the reflection from the subserosal layer with the result that the peak representing the subserosal layer is less well defined and the bladder wall thickness is overestimated.

Figure 23:
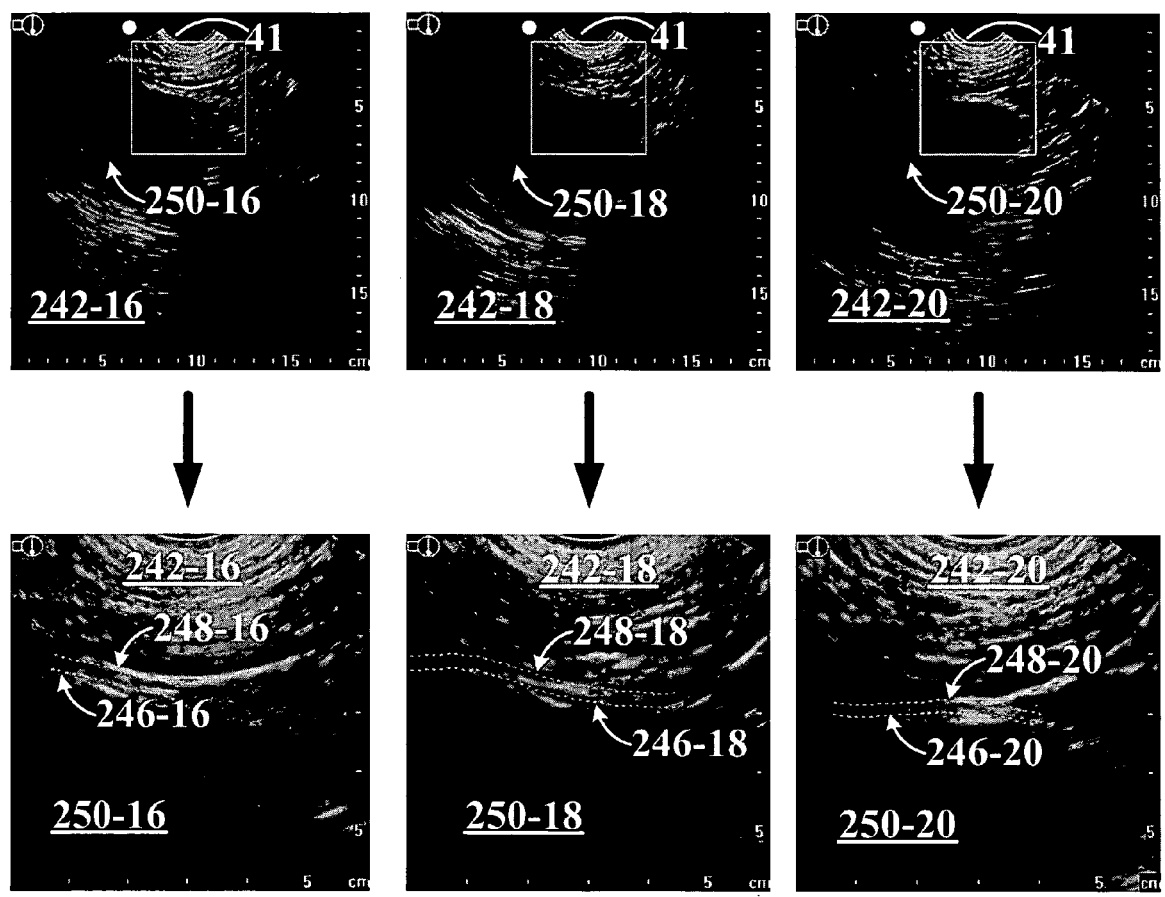
FIG. 23 are a second set of normal and magnified saggital images visualized by the ultrasound transceivers 10A-B.

FIG. 23 are a second set of normal and magnified saggital images visualized by the ultrasound transceivers 10A-B and illustrates a sample of bladder wall delineations of the anterior bladder adjacent to bladder lumens 250-16, 18, and 20 of the bladder in scan planes 242-16, 18, and 20 respectively. The upper panel of three images is near normal view. The bottom three are magnified images of the solid-line highlighted square inset. The sub-mucosal layers 246-16, 18, and 20 and sub-serosal layers 248-16, 18, and 20 of the bladder wall is depicted in dashed lines overlaid in the magnified images that represents the measured thickness of the bladder wall. The positioning of and the separation between the overlaid thickness lines is automatically determined. The saggital images are visualized so that the peritoneum and the subserosal layer of the bladder wall is automatically distinguished from each other. The delineations of the bladder wall show that thickness overestimates may occur when the perivesical tissue, such as the peritoneum, merge with the subserosal layer of the bladder wall.

Once the bladder wall thickness, t, and the surface area, S, are available, UEBW is simply calculated per equation E1:

$$UEBW = S \times t \times \rho. \quad \text{E1:}$$

The specific gravity, $\rho$, used for UEBW calculation is 0.957 as measured by Kojima et al.

Figure 24:
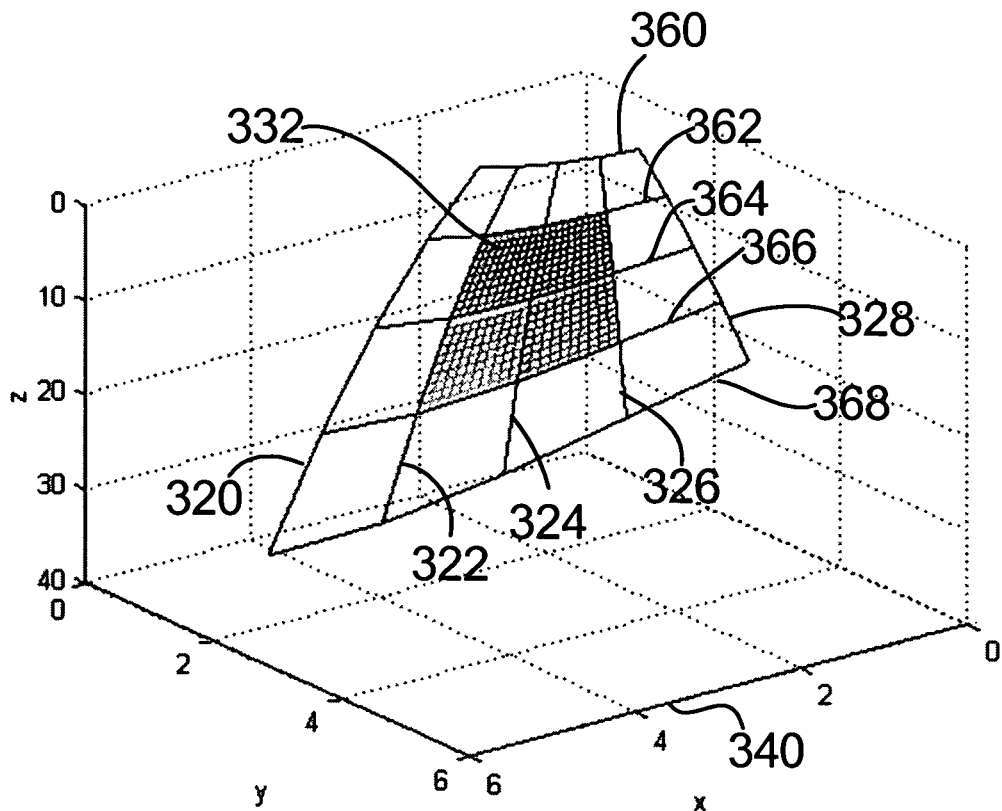
FIG. 24 is a schematic representation of four surface patch elements.

FIG. 24 is a schematic representation of four surface patch elements. Particular embodiments for the processing of the surface patch elements may be undertaken by different surface processing algorithms. For example the B-spline interpolation algorithms described in U.S. Pat. No. 6,676,605, herein incorporated by reference, or by application of the Marching Cubes algorithm as utilized from the VTK Library maintained by Kitware, Inc. (Clifton Park, N.Y., USA), also incorporated by reference herein. As depicted in three dimensions in FIG. 24, by way of example, five scan planes 320-328 are seen transmitted substantially longitudinally across a subserosal wall location 332 referenced to a tri-axis plotting grid 340. The five scan planes include the first scan plane 320, the second scan plane 322, the third scan plane 324, the fourth scan plane 326, and the fifth scan plane 328. The scan planes are represented in the preceding formulas as subscripted variable j. Substantially normal to the five longitudinal scan planes are five latitudinal integration lines 360-368 that include a first integration line 360, a second integration line 362, a third integration line 364, a fourth integration line 366, and a fifth integration line 368. The integration lines are represented in the preceding formulas as subscripted variable i.

The four surface patch functions are highlighted in FIG. 24 as the subserosal wall location 372. The i and j subscripts mentioned previously correspond to indices for the lines of latitude and longitude of the bladder surface. For the purposes of this discussion, i will correspond to lines of longitude and j will correspond to lines of latitude although it should be noted the meanings of i and j can be interchanged with a mathematically equivalent result. Using the scan plane and integration line definitions provided in FIG. 20, the four surface patch functions are identified, in the clockwise direction starting in the upper left, as $s_{322,362}$, $s_{324,362}$, $s_{324,364}$, and $s_{322,364}$.

The surface patches are defined as functions of the patch coordinates, $s_{i,j}(u,v)$. The patch coordinates u and v, are defined such that $0 \leq u, v < 1$ where 0 represents the starting latitude or longitude coordinate (the i and j locations), and 1 represents the next latitude or longitude coordinate (the i+1 and j+1 locations). The surface function could also be expressed in Cartesian coordinates where $s_{i,j}(u,v) = x_{i,j}(u,v)i + y_{i,j}(u,v)j + z_{i,j}(u,v)k$ where i, j, k, are unit vectors in the x-, y-, and z-directions respectively. In vector form, the definition of a surface patch function as given in Equation 1 above describes k, are unit vectors in the x-, y-, and z-directions respectively as shown in the equation below. In vector form, the definition of a surface patch function is given in equation E2.

$$s_{i,j}(u, v) = \begin{bmatrix} x_{i,j}(u, v) \\ y_{i,j}(u, v) \\ z_{i,j}(u, v) \end{bmatrix} \quad \text{E2}$$

With the definitions of surface patch functions complete, attention can turn to the surface area calculation represented in the fifth block 206-10 of FIG. 20. The surface area of S, A(S), can be defined as the integral of an area element over the surface S, as shown in equation E3.

$$A(S) = \int_S dA \quad \text{E3}$$

Since S is composed of a number of the patch surface functions, the calculation for the area of the surface S can be approximated as the sum of the areas of the individual surface patch functions as in equation E4.

$$A(S) = \sum_{i,j} A(s_{i,j}). \quad \text{E4}$$

The area of the surface patch is the integration of an area element over the surface patch, as shown in equation E5.

$$A(s_{i,j}) = \int_{s_{i,j}} dA_{i,j} \quad \text{E5}$$

Figure 25:
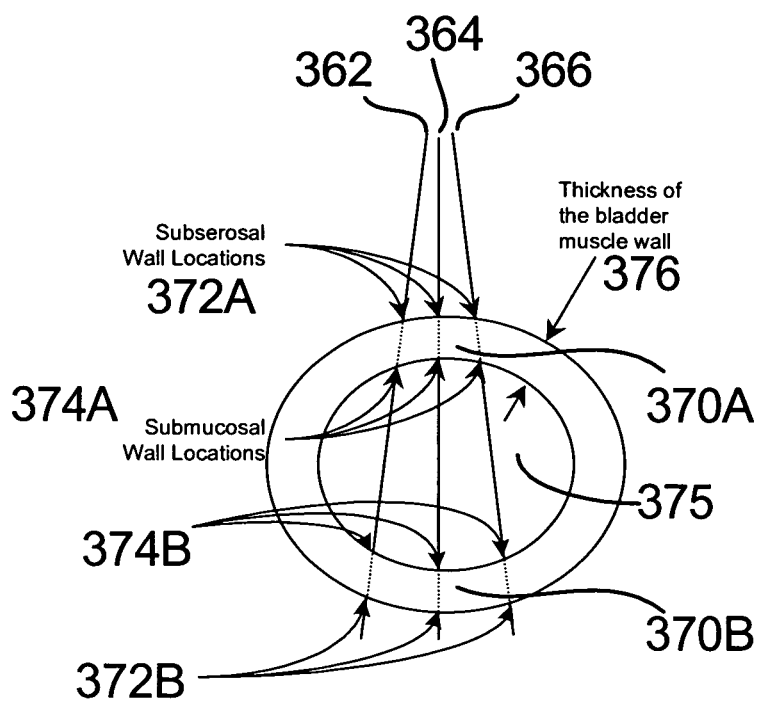
FIG. 25 is a schematic representation of three scan lines passing through the sub-serosal and sub-mucosal wall locations of an organ.

FIG. 25 is a schematic representation of three scan lines passing through the subserosal and submucosal wall locations of an organ, here illustrated for a bladder. Three scan lines 362, 364, and 366 penetrate the bladder. The dotted portion of the lines represents the portion of the scan lines that passes through the bladder muscle wall at an anterior or front wall location 370A and a posterior or back wall location 370B. The first 362, the second 364, and the third 366 scan lines are shown transmitting through the front subserosal wall location 372A and front submucosal wall location 374A. Similarly, the first 362, the second 364, and the third 366 scan lines are shown transmitting across the internal bladder region 375 and through the back submucosal wall location 374B and back submserosal wall location 372B. The front and back subserosal locations 372A and 372B occupy an outer bladder wall perimeter and the front and back submucosal locations 374A and 374B occupy an inner bladder wall perimeter. A bladder wall thickness value 376 is obtained for the respective differences along each scan line 362-366 between the subsersosal wall locations 372A and the submucosal wall locations 374A, or the subserosal wall locations 372B and the submucosal wall locations 374B. The maximum, minimum and mean values of these thicknesses are used in the bladder wall mass calculation and historical tracking of data. In a selected embodiment, the bladder is assumed to have a uniform wall thickness, so that a mean wall thickness value is derived from the scanned data and used for the determination of the bladder lumen volume 375. Although three scan lines are shown in a plane, which are separated by 7.5 degrees from each other. Both the number of scan lines in the plane and the angles separating each scan line within a plane may be varied.

Once the bladder wall thickness and the inner and outer surface area have been measured, the volume of an organ internal region such as the bladder lumen 375 may be calculated by the determining the respective differences between the front and back submucosal wall locations 374A and 374B along each scan line penetrating the bladder lumen 375. The difference between the front and back submucosal wall locations 374A and 374B defines an inter-submucosal distance. The internal volume of the bladder lumen 375 is then calculated as a function of the inter-submucosal distances of the penetrating scan lines and the area of the subserosal boundary or internal bladder perimeter. The volume of bladder lumen 375 is assumed to be the surface area times a function of the inter-submucosal distances, where the assumption is further based on a uniform wall subserosal boundary at all points around the internal bladder perimeter. In the embodiment shown, this volume calculation corresponds to the eighth block 206-20 of FIG. 19.

The methods to obtain the wall-thickness data, the mass data, and the volume of bladder lumen 375 via downloaded digital signals can be configured by the microprocessor system for remote operation via the Internet web-based system. The Internet web-based system ("System For Remote Evaluation Of Ultrasound Information Obtained By A Program Application-Specific Data Collection Device") is disclosed in detail in U.S. Pat. No. 6,569,097 to Gerald McMorrow et al., herein incorporated by reference. The internet web-based system has multiple programs that collect, analyze, and store organ thickness and organ mass determinations. The alternate embodiment thus provides an ability to measure the rate at which internal organs undergo hypertrophy with time and permits disease tracking, disease progression, and provides educational instructions to patients.

Figure 26:
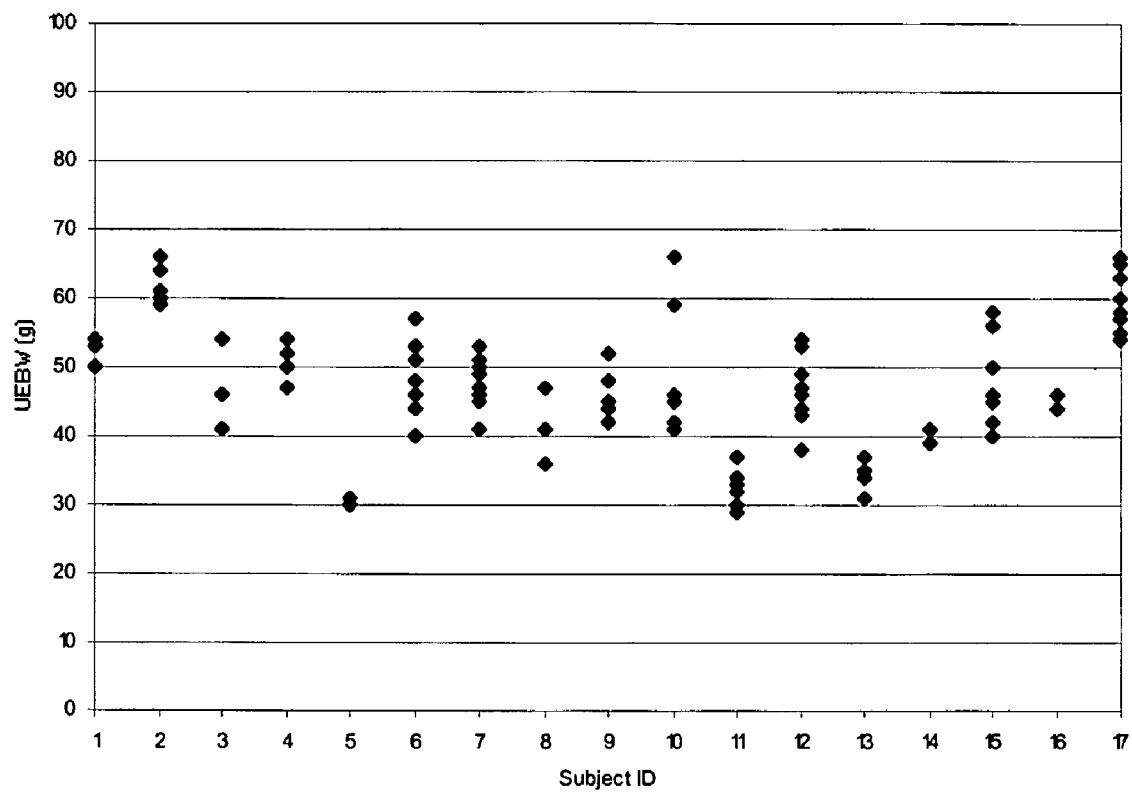
FIG. 26 depicts UEBW measurements for a subject group.
Figure 27:
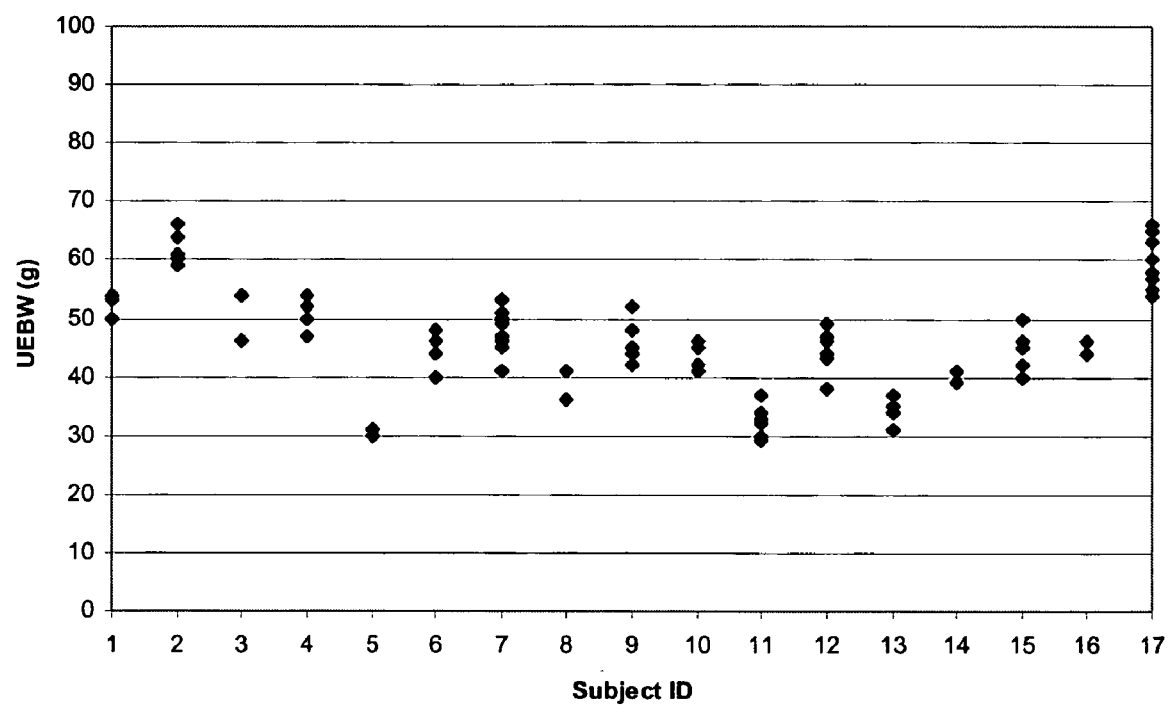
FIG. 27 depicts UEBW measurements for the subject group after excluding cases where the peritoneum merged with the subserosal layer of the bladder wall.
Figure 28:
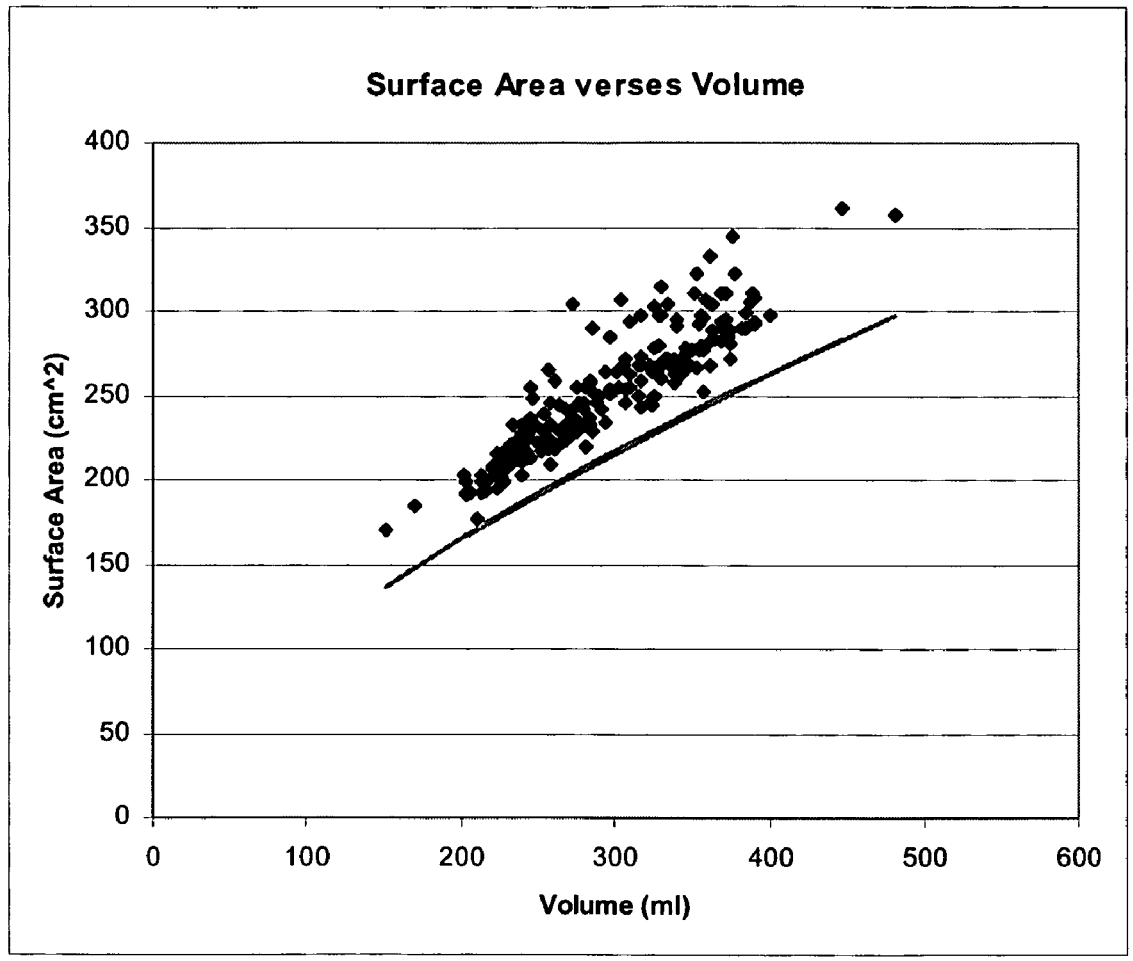
FIG. 28 shows the bladder surface area calculated by particular method embodiments plotted against the bladder volume.

FIGS. 26-28 illustrates in tabular and graphic form the UEBW determinations from seventeen healthy male subjects between the ages of 24 and 55. Each subject was scanned during two or three visits within a period of one week. A registered ultrasonographer scanned each subject with three different BVM6500 devices. The sonographer also scanned the subjects with a freehand translatable ultrasound transceiver using a 10-5 Mhz linear array probe. The bladder wall thickness was manually measured on transverse and on sagittal images on the freehand translation ultrasound probe from the leading edge of subserosal layer to the leading edge of the submucosal plus mucosal layer. The subject then voided into a uroflow device to measure the total voided volume. Finally, the post-void residual volume (PVR) was measured using the same three BVM6500 devices. All scans which were outside the specified 200 ml to 400 ml volume range were rejected from the analysis. Also, based on aiming arrow information all scans that did not produce well-centered or well-aimed images were also rejected from the analysis. By visual inspection, all cases where the peritoneum merged with the subserosal layer of the bladder were also identified.

FIG. 26 depicts UEBW measurements for a 17 member subject group. Particular embodiments measured the average UEBW on healthy male subjects to be 46 g with a standard deviation of 8.5 g between the various subjects on a total of 103 exams. FIG. 7 shows the actual UEBW measurements for the different subjects. The UEBW was found to be fairly consistent across a single subject at different volumes between 200 ml and 400 ml and between different instruments. The average coefficient of variation (the standard deviation divided by the mean) in the UEBW measurement was 8% and ranged between 2% to 19% for the different subjects. When calculating UEBW by multiplying the thickness measured by the sonographer using the freehand translation ultrasound machine and the surface area measured by the particular embodiments of UEBW device, an average coefficient of variation of 11% was found, indicating a somewhat lower consistency in manual measurement of thickness.

FIG. 27 depicts UEBW measurements for the subject group after excluding cases where the peritoneum merged with the subserosal layer of the bladder wall. Of the 17 subjects, 11 visually identified cases were excluded where the peritoneum merged with the subserosal layer. Of these 11, the average coefficient of variation in the UEBW measurement dropped to 6% with a minimum of 2% and a maximum of 9%. A plot of the remaining 92 UEBW measurements for the 17 subjects is also shown in FIG. 8.

FIG. 28 shows the bladder surface area calculated by particular method embodiments plotted against the bladder volume. The bladder surface area calculated by the methods of the particular embodiments and plotted against the bladder volume. The gray line in the figure shows the bladder surface area if it is assumed the bladder to be a spherical structure. The bladder surface area calculated by the particular embodiments of the method is on an average 18% higher (p value<0.001, minimum of 3% and maximum of 67%) than the surface area calculated under the spherical assumption, indicating that, as expected, the bladder surface cannot be well approximated by a sphere.

The pre-void bladder volume measured by the particular embodiments of the device was compared to the sum of the uroflow measured voided volume and the post-void residual. A mean difference of −4.6% (95% confidence interval, CI, of −2.7% to −6.4%) was found in the volume measurement which corresponds to a difference of −17 ml (95% CI of −11 to −23).

The particular embodiments provide an automatic and convenient method to estimate UEBW. The results show that UEBW can be consistently and accurately determined using 3-D V-mode® ultrasound. The accuracy and reproducibility improve when the 3D ultrasound scan is well centered and the bladder volume is between 200 and 400 ml. Aiming information and bladder volume measurement is provided immediately to the user to acquire the optimal scan.

Although several researchers have previously proposed the measurement of UEBW, their methods have had several limitations that the particular embodiments overcome. The accuracy of existing methods to estimate bladder weight is limited because of the assumption that the bladder is spherical in shape. The particular embodiments provide results that show the bladder to be significantly non-spherical in shape. In addition, since in the existing methods, the thickness is measured manually, the bladder wall measurements suffer from high inter-and intra-observer variability. Moreover, such measurements in everyday practice are difficult due to both the requirement of filling the patient's bladder to a known fixed volume using a catheter and the required availability of an expensive high-resolution B-mode ultrasound machine and an ultrasound technician. The particular embodiments are non-invasive, accurate, reliable and easy to use.

The 8% average coefficient of variability, CV, in UEBW found using the particular embodiments of the method results from a combination of several sources of variability which need to be studied further. Errors in surface area and thickness measurements are two of the possible sources of variability. Differences between the three devices used are another possible source of variability. Yet another source of variability is due to diurnal variations in the actual bladder weight. Yet another possible source of variability is the bladder weight itself, as measured by the particular embodiments of the method, may not be constant at all bladder volumes.

The particular embodiments provides average UEBW measurements for normal subjects to be somewhat higher than the 35 grams average value reported by Kojima et al. This difference may be explained by their assumption of a spherically shaped bladder imposed by Kojima. The actual bladder shape is significantly different from a sphere and using the actual surface area will lead to a UEBW measurement that is at least 18% higher. A second reason for the difference between their UEBW measurements and the particular embodiments may be the method of measuring thickness. The particular embodiments measure wall thickness by measuring the distance between the visible peaks in the sub-mucosal plus mucosal layer and the subserosal layer. Kojima et al. however, measure bladder wall thickness via a leading-to-leading edge distance. This leading-to-leading edge distances contributes to some differences of bladder weight.

The particular embodiments provide for an automatic, convenient, and consistent method to estimate UEBW as a diagnostic marker for bladder outlet obstruction problems. Ultrasound-estimated bladder weight (UEBW) has the potential to become an important indicator for the diagnosis of bladder outlet obstruction (BOO). The various embodiments established an approach to accurately, consistently, conveniently, and non-invasively measure UEBW using three-dimensional ultrasound imaging. A three-dimensional (3D) image of the bladder is acquired using a hand-held ultrasound machine. The infravesical region of the bladder is delineated on this 3D data set to enable the calculation of bladder volume and the bladder surface area. The outer anterior wall of the bladder is delineated to enable the calculation of the bladder wall thickness (BWT). The UEBW is measured as a product of the bladder surface area, the BWT, and the bladder muscle specific gravity. The UEBW was measured on 17 different healthy subjects and each subject was imaged several times at different bladder volumes to evaluate the consistency of the UEBW measurement. Our approach measured the average UEBW on healthy subjects to be 46 g ($\sigma$=8.5 g). The UEBW was found to be fairly consistent with an average coefficient of variability of 8% across a single subject at different bladder volumes between 200 ml and 400 ml. Our surface area measurements show that the bladder shape is significantly non-spherical.

While the particular embodiments have been illustrated and described, many changes can be made without departing from the spirit and scope of the invention. For example, the particular embodiments are not limited to rotational array scan planes, but may also include scan planes configured in wedge arrays and translational arrays. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A method of determining organ wall mass, comprising:
    positioning an ultrasound transceiver exterior to a patient such that at least a portion of the organ wall is viewable by the transceiver;
    transmitting radio frequency ultrasound pulses and receiving echoic pulses corresponding to the transmitted pulses echoed back from eternal and internal surface portions of the organ wall; and
    calculating for the portion of the organ wall at least one of
        a surface area of the external and internal surfaces of the organ wall;
        a thickness between the surfaces; and
        a mass between the surfaces.

2. The method of claim 1, wherein calculating the organ wall is delineated in a 3-D depiction.

3. The method of claim 2, wherein calculating the surface area is determined by a marching cubes algorithm applied to the 3-D depiction.

4. The method claim 3, wherein determining 3-D depiction includes an array of 2-D scan planes and an array of 3-D distributed scan lines.

5. The method claim 1, wherein positioning the transceiver generates ultrasound pulse echoes that are substantially normal to the organ wall.

6. The method of claim 5, wherein the organ wall is a bladder wall.

7. The method of claim 6, wherein the bladder contains approximately between 200 and 400 ml fluid.

8. The method of claim 7, wherein the weight of the bladder wall is calculated as a product of the inner wall surface area, the wall thickness, and the density of the wall.

9. The method of claim 7, wherein the weight of the bladder wall is calculated as a product of the outer wall surface area, the wall thickness, and the density of the wall.

10. A system to determine organ wall mass comprising:
    an ultrasound transceiver placed exterior to a patient such that at least a portion of the organ wall is viewable by the transceiver to receive radio frequency ultrasound pulses from the transceiver and to collect ultrasound echoes returning from the organ wall; and
    a microprocessor in communication with the transceiver, the microprocessor being operable to execute programs to process information from the echoes to determine an organ surface area and an organ mass.

11. The system of claim 10, wherein the organ wall is delineated in a 3-D depiction.

12. The system of claim 10, wherein the surface area is determined by a marching cubes algorithm applied to the 3-D depiction.

13. The system of claim 10, wherein the 3-D depiction includes an array of 2-D scan planes and an array of 3-D distributed scan lines.

14. The system of claim 10, wherein the ultrasound echoes are substantially normal to the organ wall.

15. The system of claim 10, wherein the organ wall is a bladder wall.

16. The system of claim 15, wherein the bladder contains a volume of fluid between approximately 200 and approximately 400 ml.

17. The system of claim 10, wherein the organ surface layer includes an inner surface area, and wherein a weight of a bladder wall is a product of the inner surface area, a wall thickness, and a density of the wall.

18. The system of claim 10, wherein the organ surface layer includes an outer surface area, and further wherein a weight of the bladder wall is a product of the outer surface area, a wall thickness, and a density of the wall.

19. The system of claim 10, wherein the transceiver further includes an inertial reference system to determine location coordinates of the transceiver in relation to the patient.

20. The system of claim 19, wherein the inertial reference system includes at least one accelerometer and at least one gyroscope.

21. A machine-executable method of determining organ wall mass of an organ exposed to ultrasound energy, comprising:
    extracting organ wall information from signals generated from ultrasound echoes returning from the organ using computer-readable medium having computer-executable instructions for determining from the organ wall information at least one of:
        a surface area of the external and internal surfaces of the organ wall;
        a thickness between the surfaces; and
        a mass between the surfaces.

22. A computer-readable medium having computer-executable instructions for performing a method of determining measurements of an organ exposed to ultrasound energy, the method comprising:
    extracting organ wall information from signals generated from ultrasound echoes returning from the organ using computer-readable medium having computer-executable instructions for determining from the organ wall information at least one of:
        a surface area of the external and internal surfaces of the organ wall;
        a thickness between the surfaces; and
        a mass between the surfaces.

23. A server having tangible computer-readable media in signal communication with computers in signal communication with an ultrasound transceiver exposing an organ to ultrasound energy, the server having executable instructions for performing a method comprising:
    receiving ultrasound echoes returning from the organ by the transceiver;
    extracting organ wall information from signals generated from the ultrasound echoes returning from the organ using the computer-readable medium having instructions executable by the microprocessor for determining from the organ wall information at least one of:
        a surface area of the external and internal surfaces of the organ wall;
        a thickness between the surfaces; and
        a mass between the surfaces.

24. The method of claim 23, wherein the organ is a bladder.

25. In a computer system having a graphical user interface including a display in signal communication with an ultrasound transceiver exposing an organ to ultrasound energy, a method of determining organ characteristics comprising:
    receiving ultrasound echoes returning from the organ by the transceiver and placing an image of the organ on the display from information obtained from the echoes;
    viewing the display to determine if the organ is approximately centered, and if centered
    extracting organ wall information from signals using tangible computer-readable medium having instructions executable by the computer system for determining from the organ wall information at least one of:
        a surface area of the external and internal surfaces of the organ wall;
        a thickness between the surfaces; and
        a mass between the surfaces.

26. The method of claim 25, wherein if the organ is not approximately centered:
    repositioning the transceiver;
    re-exposing the organ to ultrasound energy;
    receiving second ultrasound echoes returning from the re-exposed organ and placing a second image of the organ on the display from information obtained from the second echoes;
    viewing the display to determine if the re-exposed organ is approximately centered, and if centered
    extracting organ wall information from signals using tangible computer-readable medium having instructions executable by the computer system for determining from the organ wall information at least one of:
        a surface area of the external and internal surfaces of the organ wall;
        a thickness between the surfaces; and
        a mass between the surfaces.

27. The method of claim 26, wherein the organ is delineated on the display in a 3-D depiction.

* * * * *